US007455966B1

(12) United States Patent
Schaudies et al.

(10) Patent No.: US 7,455,966 B1
(45) Date of Patent: Nov. 25, 2008

(54) SYSTEM AND METHOD FOR DETECTING A BIOLOGICAL ENTITY IN A WATER SAMPLE

(75) Inventors: R. Paul Schaudies, Rockville, MD (US); Doreen A. Robinson, Laurel, MD (US)

(73) Assignee: Science Applications International Corporation, San Diego, CA (US)

( * ) Notice: Subject to any disclaimer, the term of this patent is extended or adjusted under 35 U.S.C. 154(b) by 375 days.

(21) Appl. No.: 10/271,076

(22) Filed: Oct. 15, 2002

Related U.S. Application Data

(63) Continuation-in-part of application No. 09/563,038, filed on May 1, 2000, now abandoned.

(60) Provisional application No. 60/328,826, filed on Oct. 15, 2001.

(51) Int. Cl.
*C12Q 1/68* (2006.01)
*C07H 21/04* (2006.01)
*C12P 19/34* (2006.01)

(52) U.S. Cl. .................. 435/6; 435/91.2; 536/24.32; 536/24.33

(58) Field of Classification Search .............. 435/6, 435/91.2; 536/24.33, 24.32
See application file for complete search history.

(56) References Cited

U.S. PATENT DOCUMENTS

| 5,043,272 | A | | 8/1991 | Hartley ..................... 435/91 |
| 5,106,727 | A | | 4/1992 | Hartley et al. .................. 435/6 |
| 5,298,392 | A | * | 3/1994 | Atlas et al. ..................... 435/6 |
| 5,632,957 | A | | 5/1997 | Heller et al. ............... 422/68.1 |
| 5,773,210 | A | | 6/1998 | Crowl et al. .................... 435/5 |
| 5,800,992 | A | | 9/1998 | Fodor et al. .................... 435/6 |
| 5,821,060 | A | | 10/1998 | Arlinghaus et al. ............ 435/6 |
| 5,837,832 | A | | 11/1998 | Chee et al. ................. 536/22.1 |
| 5,858,659 | A | | 1/1999 | Sapolsky et al. ............... 435/6 |
| 5,858,661 | A | | 1/1999 | Shiloh ........................... 435/6 |
| 5,861,242 | A | | 1/1999 | Chee et al. ..................... 435/5 |
| 5,871,928 | A | | 2/1999 | Fodor et al. .................... 435/6 |
| 5,925,522 | A | | 7/1999 | Wong et al. .................... 435/6 |
| 5,925,525 | A | | 7/1999 | Fodor et al. .................... 435/6 |
| 5,929,208 | A | | 7/1999 | Heller et al. ................. 530/333 |
| 5,994,058 | A | | 11/1999 | Senapathy ..................... 435/6 |
| 6,013,440 | A | | 1/2000 | Lipshutz et al. ................ 435/6 |
| 6,027,880 | A | | 2/2000 | Cronin et al. .................. 435/6 |
| 6,087,104 | A | * | 7/2000 | Yamada et al. ................. 435/6 |
| 6,156,502 | A | | 12/2000 | Beattie .......................... 435/6 |
| 7,070,935 | B2 | * | 7/2006 | Schaudies et al. ............. 435/6 |
| 2004/0096879 | A1 | * | 5/2004 | Schaudies et al. ............. 435/6 |

FOREIGN PATENT DOCUMENTS

| EP | 0 950 720 | | 10/1999 |
| WO | WO 96/41893 | | 12/1996 |
| WO | WO 9722720 A1 | * | 6/1997 |
| WO | WO 9918241 A1 | * | 4/1999 |
| WO | WO 99/22023 | | 5/1999 |
| WO | WO 02/061659 | | 8/2002 |

OTHER PUBLICATIONS

Bej et al. Multiplex PCR amplification and immobilized capture probes for detection of bacterial pathogens and indicators in water. Mol. Cell. Probes, vol. 4, pp. 353-365, 1990.*
Peng et al. Multiple PCR analyses on trace amounts of DNA extracted from fresh and paraffin wax embedded tissues after random primer PCR amplification. J. Clin.Pathol., vol. 47, pp. 605-608, 1994.*
Seto et al. Overlapping redundant seplets identical with regulatory elements of HIV and SV40. Nucleic Acids Res., vol. 17, No. 7, pp. 2783-2800, 1989.*
Nelson et al. The limits of random fingerprinting. Genomics, vol. 40, p. 1-12, 1997.*
Nelson et al. The limits of random fingerprinting. Genomics, vol. 40, p. 1-12, 1997.*
Paulson et al. Loss of heterozygosity analysis using whole genome amplification, cell sorting, and fluorescence-based PCR. Genome research, vol. 9, pp. 482-491, 1999.*
Nelson et al. The limits of random fingerprinting. Genomics, vol. 40, p. 1-12, 1997.*
International Search Report for Application No. PCT/US01/04104 dated May 6, 2002 (mailing date).
Guschin, Dmitry Y., et al., "Oligonucleotide Microchips as Genosensors for Determinative and Environmental Studies in Microbiology", *Applied and Environmental Microbiology*, vol. 63, No. 6, pp. 2397-2402, Jun. 1997.
Kahl Gunter, "Dictionary of Gene Technology," VCH Publishers, Inc., New York, NY (USA), Jun. 1995.
Boehringer Mannheim, "1998 Biochemical Catalog," GmbH printed in Germany, 8 pp., Jan. 1998.
Bej, et al., "Multiplex PCR amplification and immobilized capture probes for detection of bacterial pathogens and indicators in water," *Molecular and Cellular Probes*, vol. 4, pp. 353-365, Dec. 1990.
Hacia, J.G., et al., "Strategies for Mutational Analysis of the Large Multiexon ATM Gene Using High Density Oligonucleotide Arrays," *Genome Research*, vol. 8, pp. 1245-1258, 1998.
Telenius, et al., "Degenerate oligonucleotide primed PCR: General amplification of target DNA by a single degenerate primer," *Genomics*, vol. 13, pp. 718-725, 1992.
Sayada, et al., "Genomic fingerprinting of Yersinia enterocolitica species by degenerate oligonucleotide primed polymerase chain reaction," *Electrophoresis*, vol. 15, pp. 562-565, 1994.

(Continued)

*Primary Examiner*—Suryaprabha Chunduru
(74) *Attorney, Agent, or Firm*—King & Spalding LLP

(57) ABSTRACT

The invention relates to the detection of a biological entity in a sample. More particularly, the invention relates to detection of specific pathogens from a possible presence of hundreds to thousands of distinct biological species. The invention provides new assays that can detect the presence of one or more biological entity in a sample out of a possible number of hundreds to thousands of distinct biological species. The method according to the invention for detecting a biological entity in a sample comprises randomly amplifying nucleic acids in the sample to produce labeled nucleic acids; hybridizing the labeled nucleic acids to an array of predetermined nucleic acids; and detecting the labeled nucleic acids that have hybridized to the array.

21 Claims, 1 Drawing Sheet

OTHER PUBLICATIONS

Muller et al., "Defining ancestral karyotype of all primates by multidirectional chromosome painting between tree shrews, lemurs and humans," *Chromosoma*, vol. 108, pp. 393-400, 1999.

Ramsay, G., "DNA Chips: State-of-the Art," *Nature Biotechnology*, vol. 16, pp. 40-44, 1998.

Written Opinion for Application No. PCT/US01/04104, dated May 30, 2003 (mailing date).

Iyer, L., et al., "Adaptations of the Helix-Grip Fold for Ligand Binding and Catalysis in the START Domain Superfamily," *Proteins: Structure, Function, and Genetics*, vol. 43, pp. 134-144 (2001).

Kitazoc, Y., et al., "A New Theory of Phylogeny Inference Through Construction of Multidimensional Vector Space," *Mol. Biol. Evol.*, vol. 18, No. 5, pp. 812-828 (2001).

Geourjon, C., et al., "Identification of Related Proteins With Weak Sequence Identity Using Secondary Structure Information," *Protein Science*, vol. 10, pp. 788-797 (2001).

Anantharaman, V., et al., "Regulatory Potential, Phyletic Distribution and Evolution of Ancient, Intracellular Small-Molccule-Binding Domains," *J. Mol. Biol.*, vol. 307, pp. 1271-1292 (2001).

Liberles, D., et al., "The Adaptive Evolution Database (TAED)," *Genome Biology*, vol. 2, No. 4, pp. preprint/0003.1-0003.18.

Tatusov, R., et al., "The COG Database: New Developments in Phylogenetic Classification of Proteins From Complete Genomes," *Nucleic Acids Research*, vol. 29, No. 1, pp. 22-28 (2001).

Anantharaman, V ., et al., "TRAM, a Predicted RNA-Binding Domain, Common to tRNA Uracil Methylation and Adenine Thiolation Enzymes," *FEMS Microbiology Letters*, vol. 197, pp. 215-221 (2001).

Liu, Q., et al., "DNA Computing on Surfaces," *Nature*, vol. 403, pp. 175-179, Jan. 13, 2000.

Woese, Carl R., "Interpreting the Universal Phylogenetic Tree," *Proc. Natl. Acad. Sci.*, vol. 97, No. 15, pp. 8392-8396, Jul. 18, 2000.

Aravind, L., et al., "The a/β Fold Uracil DNA Glycosylases: A Common Origin With Diverse Fates," *Genome Biology*, vol. 1, No. 4, pp. research0007.1-0007.8 (2000).

Natale, D., et al., "Towards Understanding the First Genome Sequence of a Crenarchaeon by Genome Annotation Using Clusters of Orthologous Groups of Proteins (COGs)," *Genome Biology*, vol. 1, No. 5, pp. research0009.1-0009.19 (2000).

Grech, A., et al., "Complete Structural Characterisation of the Mammalian and *Drosophila* TRAF Genes: Implications for TRAF Evolution and the Role of Ring Finger Splice Variants," *Molecular Immunology*, vol. 37, pp. 721-734 (2000).

Head, S. R., et al., "Solid-Phase Sequence Scanning for Drug Resistance Detection in Tuberculosis," *Molecular and Cellular Probes*, vol. 13, pp. 81-87 (1999).

Tang, K., et al., "Chip-Based Genotyping by Mass Spectrometry (DNA Chip/Single Nucleotide Polymorphism)," *Proc. Natl. Acad. Sci. USA*, vol. 96, pp. 10016-10020 (1999).

Adleman, Leonard, M., "Computing With DNA," *Scientific American*, vol. 279, pp. 54-61, Aug. 1998.

Hacia, J. G. et al., "Evolutionary Sequence Comparisons Using High-Density Oligonucleotide Arrays," *Nature Genetics*, vol. 18, pp. 155-158 (1998).

Hacia, J. G., et al., "Strategies for Mutational Analysis of the Large Multiexon ATM Gene Using High-Density Oligonucleotide Arrays," *Genome Research*, vol. 8, pp. 1245-1258 (1998).

Ramsay, G., "DNA Chips: State-of-the-Art," *Nature Biotechnology*, vol. 16, pp. 40-44 (1998).

Struelens, M.D., M. J., et al., "Comparative and Library Epidemiological Typing Systems: Outbreak Investigations Versus Surveillance Systems," From the Fifth International Conference on the Prevention of Infection, *Infection Control and Hospital Epidemiology*, vol. 19, No. 8, pp. 565-569 (1998).

Castellino, A. M., "When the Chips are Down," *Genome Research*, vol. 7, pp. 943-946 (1997).

Wallraff, G., et al., "DNA Sequencing on a Chip (This Method, Which Combined Semiconductor Manufacturing Technology with Molecular Biology, Has Been Used to Build DNA and RNA Arrays at Densities as High as $10^6$ sites/$cm^2$)," *Chemtech*, pp. 22-32, Feb. 1997.

Hacia, J. G., et al., "Detection of Heterozygous Mutations of BRCA1 Using High Density Oligonucleotide Arrays and Two-Colour Fluorescence Analysis," *Nature Genetics*, vol. 14, pp. 441-447 (1996).

Schena, S., "Genome Analysis with Gene Expression Microarrays," *BioEssays*, vol. 18, No. 5, pp. 427-431 (1996).

Adleman, Leonard, M., "Molecular Computation of Solutions to Combinatorial Problems," *Science*, vol. 266, pp. 1021-1024, Nov. 11, 1994.

Grattard, F., et al., "Arbitrarily Primed PCR, Ribotyping, and Plasmid Pattern Analysis Applied to Investigation of a Nosocomial Outbreak Due to Enterobacter Cloacoe in a Neonatal Intensive Care Unit," *Journal of Clinical Microbiology*, vol. 32, No. 3, pp. 596-602 (1994).

Caetano-Anolles, G., "Amplifying DNA With Arbitrary Oligonucleotide Primers," *PCR Methods and Applications, Cold Spring Harbor Laboratory Press*, pp. 85-94 (1993).

Caetano-Anolles, et al., "Enhanced Detection of Polymorphic DNA by Multiple Arbitrary Amplicon Profiling of Endonuclease-Digested DNA: Identification of Markers Tightly Linked to the Supermodulation Locus in Soybean," *Mol. Gen. Genet.*, vol. 241, pp. 57-64 (1993).

Caetano-Anolles, et al., "DNA Amplification Fingerprinting Using Arbitrary Oligonucleotide Primers," *Applied Biochemistry and Biotechnology*, vol. 42, pp. 189-194 (1993).

Caetano-Anolles, et al., "Primer-Template Interactions During DNA Amplification Fingerprinting With Single Arbitrary Oligonucleotides," *Mol. Gen. Genet.*, vol. 235, pp. 157-165 (1992).

Atschul, Stephen, et al., "Basic Local Alignment Search Tool," *J. Mol. Biol.*, vol. 215, pp. 403-410 (1990).

Welsh, J., et al., "Fingerprinting Genomes Using PCR with Arbitrary Primers," *Nucleic Acids Research*, vol. 18, No. 24, pp. 7213-7218 (1990).

Landegren, U., et al., *Science*, vol. 242, pp. 229-237 (1988).

Liang, W., et al., *Nucl. Acids Res.*, vol. 16, p. 3579 (1988).

Loh, et al., *Science*, vol. 243, pp. 200-217 (1988).

Noonan, K. E., et al., *Nucl. Acids Res.*, vol. 16, pp. 10366 (1988).

Mullis, K. B., et al., *Meth. Enzymol.*, vol. 155, pp. 335-350 (1987).

Mullis, K. E., et al., *Cold Spring Harb. Symp. Quant. Biol.*, vol. 51, pp. 263-273 (1986).

Feinberg, A. P., et al., *Anal. Biochem.*, vol. 132, pp. 6-13 (1983).

Maniatis, et al., *Molecular Cloning: A Lab. Manual*, Cold Spring Harbor Lab., N.Y., pp. 129 and 131 (1982).

Peng, et al., "Multiple PCR Analyses on Trace Amounts of DNA Extracted from Fresh and Paraffin Wax Embedded Tissues After Random Hexamer Primer PCR Amplification," *J. Clin Pathol.*, vol. 47, pp. 605-608, 1994.

http://www.psrast.org/soilfertfact.htm (accessed on Jun. 7, 2005).

Coyne, V. E. et al., *Molecular Biology Techniques Manual- Third Edition*.

KLP Manual, Detector™ PCR DNA Biotinylation Kit.

Neapolitan, R.E. et al., *Probabilistic Reasoning in Expert Systems: Theory and Algorithms*, New York: Wiley-Interscience; 1990.

Pearl, J., *Probabilistic Reasoning in Intelligent Systems: Networks of Plausible Inference*, San Mateo, CA; Morgan Kauffman; Chapters 2 and 3, 1988.

Rumeihart, D.E. et al., *Parallel Distributed Processing, vol. 1: Foundations*, Cambridge, MA: MIT Press; 1988.

Promega Manuel, PCR Protocols and Reference Guide, as available via the Internet as of Feb. 7, 2000.

Websites for Microarray Equipment: http://www.mjr.com; http://www.nbcs.com/index2.htm; http://www.geneticmicro.com/home.html; http://www.genomicsolutions.com/bio/bio/htm; http://www.gml-inc.com/Products/Sorvall%20RT%206000D%20.htm; http://www.biorad.com; http://order.lifetech.com/lti_store/search1b.icl; http://www.owlsci.com; http://www.alphainnotech.com/lsmaster.html; http://www.mjr.com/html/contact/index.html; http://www.pebio.com/pc/catalog2/pg32.html; http://www.pebio.com/pc/catalog2/pg34.html; http://www.savec.com; http://www.stratagene.com/instruments/stratalinker.com; http://www.robsci.com/hydra/hydra5.html, all available via the Internet.

"Random Primer DNA Labeling Mix," AppliChem, GMbH, Product Insert A3746.0025, 2pp., Apr. 1999.

Sehgal, Anil, et al., "Application of the Differential Hybridization of Atlas™ Human Expression Arrays Technique in the Identification of Differentially Expressed Genes in Human Glioblastoma Multiforme Tumor Tissue," *Journal of Surgical Oncology*, vol. 67, pp. 234-241, 1998.

Brenner, Don J., et al., "Conservation of Transfer Ribonucleic Acid and 5S Ribonucleic Acid Cistrons in Enterobacteriaceae," *Journal of Bacteriology*, vol. 129, No. 3, pp. 1435, Mar., 1977.

Kauppinen, Juha, "Mycobacterium Malmoense-Specific Nested PCR Based on a Conserved Sequence, Detected in Random Amplified Polymorphic DNA Fingerprints," *Journal of Clinical Microbiology*, vol. 37, No. 5, pp. 1454-1458, May, 1999.

* cited by examiner

SYSTEM AND METHOD FOR DETECTING A BIOLOGICAL ENTITY IN A WATER SAMPLE

CROSS-REFERENCE TO RELATED APPLICATIONS

This application claims priority to U.S. Provisional Patent Application No. 60/328,826 entitled "A NOVEL SYSTEM AND METHOD FOR DETECTING A BIOLOGICAL ENTITY IN A SAMPLE" filed on Oct. 15, 2001. Further, this application is a continuation-in-part of and claims priority to U.S. patent application Ser. No. 09/563,038 entitled "A NOVEL SYSTEM AND METHOD FOR DETECTING A BIOLOGICAL ENTITY IN A SAMPLE" filed May 1, 2000 now abandoned.

FIELD OF THE INVENTION

The invention relates to the rapid detection of a biological entity in a sample. More particularly, the invention relates to detection of specific pathogens from a possible presence of one to hundreds to thousands of pathogens.

BACKGROUND OF THE INVENTION

The events of Sep. 11, 2001, have created an pressing need for the ability to rapidly determine whether a biological signature for a pathogen is present in a sample. Crowding and unrest in the modem world has created the potential for rapid spread of terrorism and disease, either through germ warfare, or simply through disease transmission among densely packed hosts in urban environments. Wade, New York Times, Nov. 21, 199'" discloses that one gram of anthrax, about the weight of two paper clips, contains enough doses to kill ten million people. Many other pathogenic organisms could similarly be used by terrorists. Unfortunately, it is difficult to know which pathogens were being used before it was too late to avoid significant illness and death. In addition, in urban environments widespread epidemics may be more likely to happen, due to the close proximity of diseased and healthy people. In such instances, it could be critical to determine at an early stage what pathogen is involved to provide effective treatment and/or prophylaxis. Moreover, when natural disasters, such as flooding or earthquakes occur, frequently, widespread disease follows in the aftermath. Effective relief requires the ability to rapidly identify any pathogen causing such an outbreak.

Unfortunately, current methodologies do not allow rapid, simultaneous screening for specific pathogens among a possible hundreds to thousands of pathogens.

Current methodologies include antibody-based assays, DNA chip assays and assays based on polymerase chain reaction.

For example, Chee et al., U.S. Pat. No. 5,861,242 (1999) discloses an array of nucleic acid probes on biological chips for diagnosis of HIV.

Crowl et al., U.S. Pat. No. 5,773,210 (1998) discloses an assay for HIV utilizing an envelope protein from the virus to detect antibodies to the virus in patient's serum. Grattard et al., J. Clin. Microbiol. 32: 596-602 (1994) discloses the use of PCR to detected *Enterobacter cloacae* in a nosocomial outbreak.

Unfortunately, all of these methodologies are limited to the detection of a single species of pathogen. Moreover, the conventional approaches do not permit multiple analyses to be run concurrently regarding multiple biological entities in a sample. Further, conventional approaches There is, therefore, a need for new assays that can detect the presence of one or more biological entity in a sample out of a possible number of hundreds to thousands of distinct biological species.

SUMMARY OF THE INVENTION

The invention provides new assays that can detect the presence of one or more biological entities in a sample which might be any one of hundreds to thousands of possible distinct biological species. The method according to the invention for detecting a biological entity in a sample comprises randomly amplifying nucleic acids in the sample to produce labeled nucleic acids; hybridizing the labeled nucleic acids to an array of predetermined nucleic acids; and detecting the labeled nucleic acids that have hybridized to the array. The method according to the invention is useful for such detection in the context of hospitals or physicians' offices, battlefield or trauma situations, emergency responders, forensic analysis, food and water monitoring, screening for indications of genetic alterations in specific organisms and environmental analysis and background characterizations.

The present invention is useful as a phylogenetic analysis. In such embodiments a continuum of highly conserved to highly specific nucleic acids are used to categorize a multiplicity of biological entities from a single sample based upon binary pattern generated. Thus one can conclude the presence or absence of specific biological entities in the sample, as well as establish the organism's kingdom, phylum, class, order, genus species.

In preferred embodiments, the amplification step comprises a polymerase chain reaction. Preferably, the amplification step utilizes random primers four to nine nucleotides in length, most preferably four to six nucleotides in length. In certain preferred embodiments, the array of predetermined nucleic acids are immobilized on a surface. In certain preferred embodiments, the labeled nucleic acids are enzymatically detected. In certain preferred embodiments, the labeled nucleic acids are biotinylated. In certain preferred embodiments, the labeled nucleic acids are fluorescently labeled or radiolabeled. In certain preferred embodiments, the labeled nucleic acids are labeled with digoxigenin. In certain preferred embodiments, the surface on which the predetermined nucleic acids are immobilized is an opaque membrane. In certain preferred embodiments, the surface is silica-based. Preferably, the predetermined nucleic acid sequences are at predetermined positions on the array. In certain preferred embodiments the sample comprises multiple biological entities. Generally, at least one biological entity to be detected is a pathogen. In certain preferred embodiments, the predetermined nucleic acids are more than 30 nucleotides in length.

Another advantage of the present invention is the ability to characterize unknown samples and to detect genetically altered organisms, including newly have antibiotic resistance and chimeras. For example, there are reports of the construction of a chimera of vacinna and equine encephalitis. In such circumstances, if the chimera had derived its structural genes from vacinna and its pathogenic genes from equine encephalitis, then the present invention would allow one to detect the genetically altered organism.

DETAILED DESCRIPTION OF THE PREFERRED EMBODIMENTS

Figure 1:
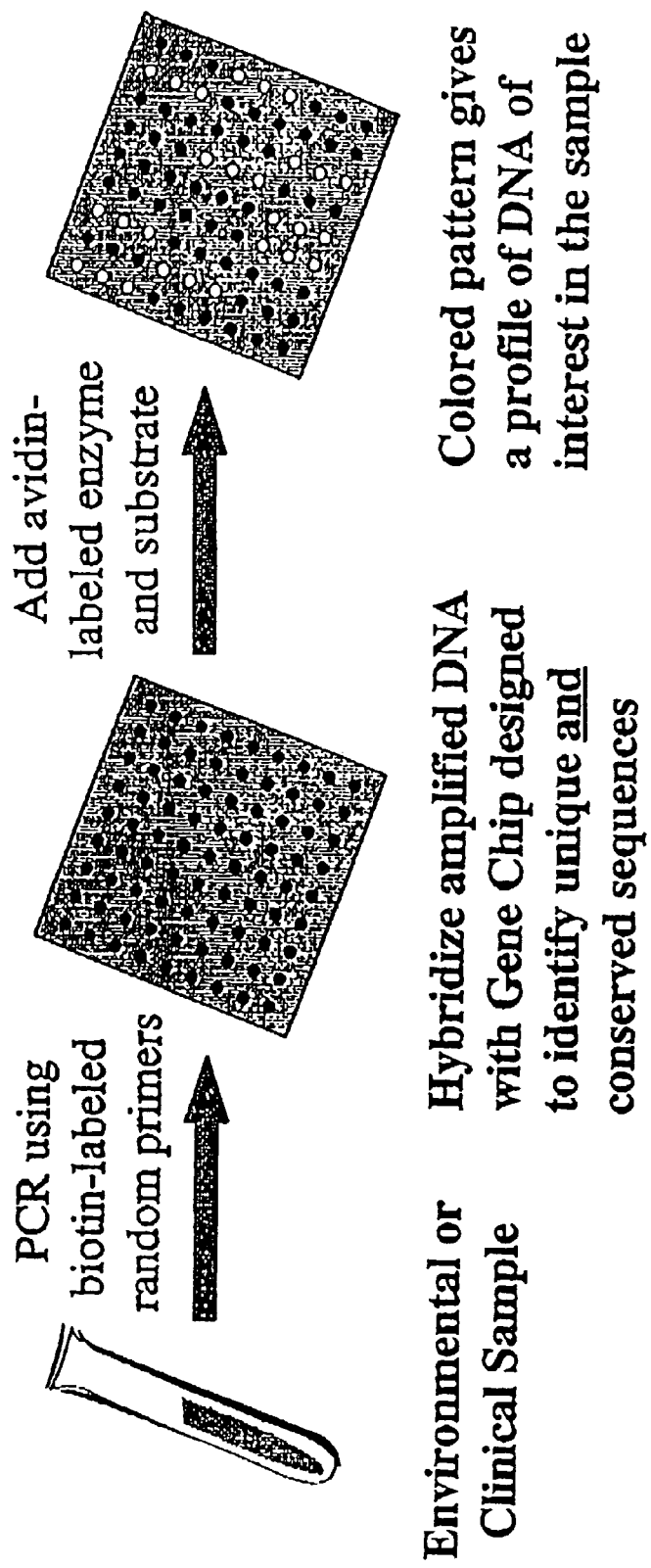
FIG. 1 shows a schematic for a preferred embodiment of the invention.

The invention relates to the detection of a biological entity in a sample. More particularly, the invention relates to detection of specific pathogens from a possible presence of hundreds to thousands of pathogens. The invention provides new assays that can detect the presence of one or more biological entity in a sample which might be any one of hundreds to thousands of possible distinct biological species.

The patents and publications recited herein reflect the level of knowledge in the field and are hereby incorporated by reference in their entirety. In the event of conflict between any such patent or publication and the present disclosure, the present disclosure shall prevail.

The method according to the invention for detecting a biological entity in a sample comprises randomly amplifying nucleic acids in the sample to produce labeled nucleic acids; hybridizing the labeled nucleic acids to an array of predetermined nucleic acids; and detecting the labeled nucleic acids that have hybridized to the array. The method according to the invention is useful for such detection in the context of hospitals or physicians' offices, battlefield or trauma situations, emergency responders, forensic analysis, food and water monitoring, screening for indications of genetic alterations in specific organisms and environmental analysis and background characterizations.

For purposes of the invention, the term "randomly amplifying" means increasing the copy number of a segment of nucleic acid in vitro using random primers, each of which are four to nine nucleotides in length, most preferably four to six nucleotides in length. "Biological entity" includes viruses, viroids, bacteria, fungi, protozoa and the like. A "sample" is any source, and can be a gas, a fluid, a solid or any mixture thereof. "Nucleic acids" means RNA and/or DNA, and may include unnatural bases. A "predetermined nucleic acid" is a nucleic acid for which the sequence is known. In certain preferred embodiments, the predetermined nucleic acids are more than 30 nucleotides in length. A "labeled nucleic acid" is a nucleic acid that can be detected. "Hybridized" means having formed a sufficient number of base pairs to form a nucleic acid that is at least partly double stranded under the conditions of detection. An "array of predetermined nucleic acids" is a multiplicity of predetermined nucleic acids (including nucleic acids complementary to a biological entity to potentially be detected) having a known spatial arrangement or relationship to each other.

In preferred embodiments, the amplification step comprises a polymerase chain reaction. Generally, conventional PCR methodology (see e.g., Molecular Biology Techniques Manual, Third Edition (1994), Coyne et al. Eds.) can be used for the amplification, except that the annealing step is preferably carried out at lower temperatures, e.g., 50-65° C. The primers utilized in the amplification step are multiple random primers of four to six nucleotides in length. Whereas longer primers are useful for the amplification of known sequences they are not suitable for the non-specific amplification of nucleic acids in a sample as long primers necessarily provide significant specificity of amplification. Use of short, random primers will allow the amplification of all nucleic acids within a given sample. Due to their short length, the primers are capable of binding to virtually all of the DNA sequences, and use of random primers (i.e. primers having different DNA sequences) further increases the likelihood that all DNA sequences will be amplified.

In certain preferred embodiments, one or more nucleoside triphosphate used in the amplification will be labeled. In certain preferred embodiments, the labeled nucleic acids are enzymatically detected. Preferred enzymes include, without limitation, alkaline phosphatase, horseradish peroxidase and any other enzyme that produces a colored product. In certain preferred embodiments, the labeled nucleic acids are biotinylated. In certain preferred embodiments, the labeled nucleic acids are fluorescently labeled or radiolabeled. In certain preferred embodiments, the labeled nucleic acids are labeled with digoxigenin. Biotinylated nucleic acid sequences are readily identified through incubation with an avidin linked calorimetric enzyme, for example, alkaline phosphatase or horse radish peroxidase. Biotin is particularly preferred in applications in which visualization is required in the absence of fluorescence-based systems. Digoxigenin labeled nucleic acid sequences are readily detected using commercially available immunological reagents. Recent advances in molecular biology, in part due to the efforts under the Human Genome Project, have spurred the development of new methods for the labeling and detection of DNA and DNA fragments. Traditionally, radioisotopes have served as sensitive labels for DNA while, more recently, fluorescent, chemiluminescent and bioactive reporter groups have also been utilized. Fluorescent and chemiluminescent labels function by the emission of light as a result of the absorption of radiation and chemical reactions, respectively. Kits and protocols for labeling the primers and/or the amplified sequences are readily available in the published literature regarding PCR amplifications. Such kits and protocols provide detailed instructions for the labeling of both primers and the amplified DNA which protocols can readily be adapted for the purposes of the method of the invention.

In certain preferred embodiments, the array of predetermined nucleic acids are immobilized on a surface. In certain preferred embodiments, the surface on which the predetermined nucleic acids are immobilized is an opaque membrane. Preferred opaque membrane materials include, without limitation, nitrocellulose and nylon. Opaque membranes are particularly preferred in rugged situations, such as battlefield or other field applications. In certain preferred embodiments, the surface is silica-based. "Silica-based" means containing silica or a silica derivative, and any commercially available silicate chip would be useful. Silica-based chips are particularly useful for hospital or laboratory settings and are preferably used in a fluorescent reader.

Preferably, the predetermined nucleic acid sequences are at predetermined positions on the array. In preferred embodiments, the predetermined nucleic acid sequences are arrayed by immobilization on a surface. Arraying the predetermined nucleic acid sequences at predetermined positions on a chip allows a chip-based approach to the detection of biological species within a given sample. The predetermined nucleic acid sequences are printed onto the chip using computer-controlled, high speed robotics, which devices are often termed "spotters". A spotter can be utilized to rapidly mass-produce identical arrays of the predetermined nucleic acid sequences on hundreds of chips. Because the location of each predetermined nucleic acid on the chip is known, hybridization, detection and localization lead to the identification of the biological entity or entities) present in the sample (see FIG. 1). In certain preferred embodiments the sample comprises multiple biological entities. Generally, at least one biological entity to be detected is a pathogen.

The invention relates to the identification of one or more biological entities in a given sample. The invention provides a method for the rapid identification of multiple biological entities simultaneously within a given sample. This contribution allows scientists, technicians and medical workers to rapidly and simultaneously identify the presence of multiple biological entities, including pathogens, in a sample taken from any source, including a human individual, a land or aquatic animal, and water, plants or foodstuffs, dirt, air, or any other environmental or forensic sample.

The method of the invention has particular application to situations of battlefield or outbreaks of disease which may be caused by a biological pathogen, as well as forensic analysis, food and water monitoring to screening for indications of genetic manipulations in specific organisms and environmental analysis and background characterizations. Using the method of the invention, any known biological pathogen could be detected in a sample, and multiple biological species can be simultaneously detected. In addition, the method is useful for the detection of biological pathogens which affect plants or animals.

The potential threat of terrorism and battlefield use of biological weapons is growing around the world. On the battlefield, multiple biological weapons may be released at one time, thus creating a situation in which field doctors should have the capability of simultaneously identify multiple biological species in a single test. Prior to applicants invention, however, no such method existed. In an urban setting, a single biological pathogen might be released over a broad area, or in a crowded location, with little or no warning as to the threat and event of this release, nor any statement as to the identity of the biological species which was released.

In either such situation referred to above, or in the event of a natural or accidental occurrence of dissemination of a biological pathogen (e.g. contamination of foodstuffs with *Eschericia coli*, or the spread of communicable diseases such as meningitis), the first indication of the infection of humans could be a cluster of individuals each displaying similar symptoms. However, as the initial symptoms of many biological pathogens are very similar to each other and to symptoms of the flu (e.g., headaches, fever, fatigue, aching muscles, coughing) the rapid identification of the actual biological species causing the symptoms would be a significant benefit such that prompt and proper treatment could be implemented by medical professionals. In addition, the method according to the resistance, thereby affording more effective treatment.

Examples of biological pathogens which may be used for production of biological weapons, or for use in terrorism in which event the goal of such terrorism may be to kill or debilitate individuals animals or plants, include, without limitation, *Bacillus anthracis* (anthrax), *Yersinia pestis* (bubonic plague), *Brucella suis* (brucellosis), *Pasturella tularensis* (tularemia), *Coxiella bumetti* (Q-fever), *Pseudomonas arenginosa* (pneumonia, meningitis), *Vibrio cholera* (cholera), Variola virus (small pox), Botulinum toxin (botulism), Saxitoxin (respiratory paralysis), *Ricinus communis* (ricin), *Salmonella, Staphylococcus aureus*, aflatoxin and other fungal toxins, *Shigella* (dysentery), and Yellow Fever Virus.

The present invention is useful as a phylogenetic analysis. In such embodiments a continuum of highly conserved to highly specific nucleic acids are used to categorize a multiplicity of biological entities from a single sample based upon binary pattern generated. Thus one can conclude the presence or absence of specific biological entities in the sample, as well as establish the organism's kingdom, phylum, class, order, genus species.

In another preferred embodiment, the sample comprises multiple (more than one) biological entities. Depending upon the type of substrate chosen and the size of the chosen substrate, a chip can be arrayed with hundreds or thousands of predetermined nucleic acids in a predetermined pattern.

In another preferred embodiment, one or more of the biological entities is a pathogen. Since the method of the invention is designed to amplify all DNA within the sample, a biological species most likely will need to be present in multiple copies in order to be sufficiently amplified. If pathological entities are present in the sample in a sufficient amount to cause harm, then they will most likely be present in multiple copies and will be sufficiently amplified through the method of the invention.

To increase the confidence in the results of the biological species detected according to the method of the invention, the array will preferably include positive and negative controls and redundancies, for example multiple copies of the same nucleic acid or several distinct nucleic acids from the same target organism. The array is also useful to provide broad as well as specific identification. For example, 16s ribosomal RNA can be used to establish the presence of bacteria, conserved *bacillus* sequences can be used to identify *bacillus* presence, and specific DNA can further classify the *bacillus* species or strain. Any desired target biological species, including pathological species, can be included in the array through reference to the published literature of the DNA sequences characteristic of such organism, and then either synthesis or cloning of such published sequences.

The presence of a particular target organism within a given sample is determined by hybridizing the labeled amplified nucleic acids from the sample to the array on the chip according to well known techniques. Hybridization should preferably be conducted under high stringency conditions, as it is expected that the amplified products will be at least 30 nucleotides in length and they are being hybridized to PCR amplified gene fragments. Suitable high stringency conditions include hybridization at between 50° C. and 65° C. Then utilizing the proper means of detection to visualize the particular label used for the labeling of the amplified nucleic acids in order to identify which predetermined nucleic acid sequences were hybridized to the amplified nucleic acids. Since the chip holds an array of predetermined nucleic acids in a predetermined pattern, the pattern of hybridization will identify the biological species within the sample.

In yet another preferred embodiment of the present invention, it will be appreciated that the present invention can also be adapted to assay for biological entities whose genetic material is RNA. This can be accomplished by using a reverse transcriptase in conjunction with the other components of the present invention.

In another preferred embodiment of the present invention, messenger RNA (mRNA) is also assayed in determining the presence of one or more biological entities. For example, a particular organism might have a gene conferring a particular antibiotic resistance, or might have a gene from a different organism. In such circumstances, in a preferred embodiment of the present invention, mRNA can be interrogated to determine the presence of the gene.

It will be appreciated that under field conditions where field personnel are seeking to rapidly determine how best to respond to an outbreak of a biological entity, the ability to assay for antibiotic resistance (or lack thereof) as measured by the present invention is more important than determining precisely which biological entity is present.

In another preferred embodiment of the present invention, the assay for mRNA would also lead to determinations as to whether certain protein targets are also being produced.

Another aspect of the present invention is the ability to assay for nonculturable bacteria. Perhaps only 1 to 10% of the bacterial species that exist on this planet have been discovered, in part, because some species are difficult to culture. The present invention permits one to identify bacteria and other biological entities which are difficult to culture.

Another aspect of the present invention is the use of the system and method of detecting biological entities in environmental monitoring. When employed in conjunction with pattern recognition elements, the present invention permits biodetection in which an environment is continuously monitored. The present invention provides an array that permits it to be replicated easily. In one preferred embodiment of the present invention, a number of arrays can be exposed sequentially at set intervals. One can monitor for changes in that pattern, and over time one can see how the background pattern might change and what organisms that look like pathogenic organisms come up in the sample.

In one preferred embodiment of the present invention, the ability to focus on conserved sequences rather than distinguishing features of biological organisms permits additional sensitivity. Conventionally, when one looks for pathogenic agents and environmental samples for example, one looks at the leaves on the phylogenetic tree, that is, they develop primer pairs that are specific to a biological entity. A preferred approach of the present invention starts at the base of the phylogenetic tree and looks for conserved sequences found in all bacterial species. In addition, the present invention also preferably provides a redundancy by analyzing DNA, RNA, mRNA message and protein, thus, providing increased confidence in the analysis. As one will appreciate this increased confidence and, most especially, the fewer false negatives will spare the population of false alarms regarding biological terrorism.

The present invention provides the ability to ask and answer thousands of questions simultaneously, which, when that combined with the phylogenetic approach, furnishes an analytic technique that does not miss things for which one doesn't have the leaves of the phylogenetic tree. Here, at the least, one can tell what biological entity is not present, because it is not represented by any of the sequences provided, but one can also determine, with a fine degree of resolution, how far up the branch of the phylogenetic tree the biological entity is.

Another preferred aspect of the present invention is the ability to provide a phenotypic profile of an individual based on their DNA. For example, with the present invention, one can assay the genes for phenotypic characteristics, such as blue eyes. With the approach of the present invention one can arrange the genes that determine certain phenotypic traits and then from a small sample of, for example, hair or semen, one could amplify that DNA and then put together a phenotypic profile.

An advantage of the present invention is the ability to run thousands of PCR reactions simultaneously, thus, allowing for the interrogation of up to for 10,000 sequences simultaneously. One will appreciate that such capability permits the construction of diagnostic kits for hemophilia, Alzheimer genes, arteriosclerosis, among others.

Another preferred aspect of the present invention is the ability to characterize individuals and their respective disease state by their internal flora. One can appreciate that certain disease states could be characterized by particular constellations of biological entities.

Additionally, certain diseases that were thought not to have a responsible biological agent are now turning out to implicate biological entities. For example, until recently stomach ulcers were not considered to have a bacterial cause, but Helicobacterium pylori has now been implicated as the causative agent in many instances of stomach ulcer. It is likely that other diseases of unknown etiobgy will turn out to have a biological entity cause. In another example, if one has congestive heart failure, their color is off and there is a change in the organisms that colonizes them. The present invention would allow for diagnostic analyses of such agents.

In another preferred embodiment of the present invention, the present invention permits analysis of the biological entities associated with the environments in which an individual resides or has spent some period of time. For example, for an individual spending time in a desert, certain mites and other kinds of organisms might be found in the individual's epithelium or hair.

In another preferred embodiment of the present invention, one can place the detection system of the present invention in communication with fluids or other samples from an individual so as to achieve real-time monitoring of the course of infection or the efficacy of a treatment. For example, one could have an array in a diagnostic device that would assay for end points in the treatment of a disease state.

It will be appreciated that the present invention preferably also includes software and logic tools for pattern recognition and rapid screening.

Further, with regard to the environmental analysis aspect, among others, of the present invention, it will be appreciated that dilution of the sample provides a determination of quantitation and allows for the detection of biological entities in only small amounts. This can be accomplished by performing a series of dilutions, such as 10×, 100×, 1000×, and 10,000× dilution, and subsequently carrying out a subtractive analysis. It will appreciated that preferably this analysis is enhanced by the use of pattern recognition and regression analysis algorithms.

It will be appreciated that another preferred aspect of the present invention is a system or kit for accomplishing the detection of biological entities in a sample, as described herein.

The following example(s) are intended to further illustrate certain preferred embodiments of the invention, and are not intended to be limiting in nature.

Example 1

Preparation of a Diagnostic Array

The following steps may be used to generate arrays of predetermined nucleic acids that are fixed to a solid surface for carrying out the method of the invention. The number of predetermined nucleic acids which are included on any array can be designed according to the specific needs and desires of the user. Relative amounts of various biological entities can be ascertained by conducting sequential hybridizations using serial dilutions of the amplified/labeled nucleic acid.

The desired collection predetermined nucleic acid sequences, each of which characterizes a different biological entity or a variant of a biological entity, are selected from various sequence databases or printed publications. Such predetermined nucleic acid sequences are then either synthesized based upon the published nucleic acid sequence or cloned from appropriate sources (such as from the biological entity containing such nucleic acid sequence or from a cDNA or genomic library containing such nucleic acid sequence). Each selected predetermined nucleic acid sequence is amplified (e.g., using PCR and a primer pair which is specific for such predetermined nucleic acid sequence) to generate a sufficient quantity of such sequence for deposit on a solid substrate (e.g. a chip) and then isolated according to any of the well known techniques for isolation of DNA so that each deposit on the solid surface is free of impurities which could lead to a false indication that such predetermined nucleic acid sequence is present in a sample which is being tested. If desired one or more predetermined nucleic acid sequences could be combined in a single deposit on the solid surface, for example it may be deemed desirable to combine one or more variants of particular biological entity.

Numerous methods for the amplification and purification of nucleic acids are publicly available. The following protocol is merely illustrative.

Materials and Equipment
PCR primers modified with a 5'-amino-modifier C6 (Glen Research #10-1906-90)
Taq DNA polymerase (Stratagene #600139)
PCR Purification Kit (TeleChem #PCR-100)
Flat-bottom 384-well plates (Nunc #242765)
Micro-Spotting Solution (TeleChem #MSS-1).
Method
1. Add 1.0 microliter of DNA (10 ng/microliter) of the desired biological species from which the predetermined nucleic acid sequence is to be prepared into a reaction container. The DNA for each desired biological species is to be amplified in a separate reaction using primers (21 mers) which are specific for the predetermined nucleic acid to be amplified.
2. Add 99.0 microliter of PCR mix which contains 10 microliter of 10×PCR buffer (500 mM KCl, 100 mM Tris-Cl pH 8.3, 15 mM Mg2+, 0.1% gelatin), microliter of dNTP cocktail (2 mM each), 1.0 microliter primer 1 (100 pmole/microliter), 1.0 microliter primer 2 (100 pmole/microliter), 1.0 microliter biological sample, 76 microliter H$_2$O, and 1.0 microliter Taq Polymerase (– units/microliter).
3. Amplify the DNA using rounds of PCR (94° C., 30 sec; 55° C., 30 sec; 72° C., 60 sec).
4. Purify the PCR products using a PCR Purification Kit.
5. Elute products with 100 microliter of 0.01×TE (pH 8.0).
6. Dry products to completion in a speedvac.
7. Resuspend each PCR product in 7.5 microliter Micro-Spotting solution.
8. Transfer to a flat bottom 384-well plate (Nunc) for arraying.
   a. Amino-linked cDNAs are made during PCR using primers that contain a C6 amino modifier (Glen Research) on the end of each primer.
   b. Plasmid DNA can be prepared by alkaline lysis and purified. The 96-well REAL prep (Qiagen #SQ81 1 and #19504) facilitates rapid preparation.

Each of the collection of predetermined nucleic acid sequences are then spotted or printed onto a silica-based substrate or opaque membrane (nylon or nitrocellulose) using an arraying machine to create an array of predetermined nucleic acid sequences in a regular grid of hundreds to thousands of spots. The DNA in the spots may need to be bonded to the substrate to keep hem from washing off during hybridization.

Numerous methods for the spotting or printing of nucleic acid sequences on a surface are publicly available. The following protocol is merely illustrative.

Reagents and Equipment

Micro-Spotting Robot (Many Models are Available)
Stealth Micro Spotting Device (TeleChem) 25 SuperAldehyde Substrates (TeleChem)
Method
1. Obtain silylated (active aldehyde) microscope slides (CEL Associates).

2. Print amino-linked cDNAs using a micro-spotting device according the to manufacturer's instructions.
3. Allow printed microarrays to dry overnight in a slide box.
4. Soak slides twice in 0.2% SUS for 2 mm at room temperature with vigorous agitation.
5. Soak slides twice in ddH$_2$O for 2 mm at room temperature with vigorous agitation.
6. Transfer slides into ddH$_2$O at 95-100° C. for 2 minutes to allow DNA denaturation.
7. Allow slides to thy thoroughly at room temperature (–5 mm).
8. Transfer slides into a sodium borohydride solution for 5 mm at room temperature to reduce free aldehydes.
9. Rinse slides three times in 0.2% SDS for 1 mm each at room temperature.
10. Rinse slides once in ddH$_2$O for I mm at room temperature.
11. Submerge slides in ddH$_2$O at 95-100° C. for 2 seconds.
12. Allow the slides to air dry and store in the dark a 25° C. (stable for >1 year).
   a. Drying increases crosslinking efficiency. Several days or more is acceptable.
   b. This step removes salt and unbound DNA.
   c. Prepare sodium borohydride solution JUST PRIOR to use as follows.
   Dissolve 1.0 g NaBH4 in 300 ml phosphate buffered saline (PBS). Add 100 ml 100% ethanol to reduce bubbling.
   d. Heating the slides greatly aids in the drying process.

Example 2

Use of a Diagnostic Array

An array, such as one prepared according to Example 1, would be utilized by preparing labeled nucleic acid from the sample to be screened, and hybridizing such labeled nucleic acid with the array. In addition labeled nucleic acid of the designated control sequences would be prepared (or in the event that the array is sold as part of a kit, could be supplied to the user).

Radioactive, calorimetric, chemiluminescent or fluorescent tags can be used for labeling of nucleic acid sequences from the sample and for the control. Numerous techniques for scanning arrays, detecting fluorescent, chemiluminescent, or colorimetric output, and analyzing results are being developed and commercialized. For example, GSI Lumonics has developed low-cost, high-throughput 2-, 3-, and 4-color laser scanning systems (ScanArray Systems). Numerous protocols for the preparation of labeled nucleic acid sequences are publicly available. The following protocols are provided for illustrative purposes: (i) a method for hybridization of fluorescently labeled sample to an array and analysis of the biological entities, (ii) a method of preparing fluorescently labeled nucleic acid from a sample and (iii) preparation of fluorescently labeled control nucleic acids.

1. Hybridization of Labeled Sample Nucleic Acid to Arrays and Analysis of Biological Entities Reagents and Equipment
Hybridization cassettes (TeleChem)
Array wash station (TeleChem)
Fluorescent labeled DNA derived from sample to be tested
Fluorescent labeled control nucleic acid sequences
ScanArray 3000, 4000 or 5000 (GSI Lumonics)

Method
1. Place the array in a hybridization cassette. The array used in this example is a microarray that is 22×22 mm in size.
2. Add 5.0 microliter of 5×SSC+0.2% SDS to the slot in the cassette for humidification.
3. Pipette 6.0 microliter of fluorescent labeled nucleic acids derived from the sample, including a sufficient concentration of fluorescent labeled control nucleic acid, along the edge of a 22×22 mm cover slip.
4. Place the cover slip onto the microarray using forceps such that the sample forms a thin monolayer between the cover slip and the microarray.
5. Seal the hybridization cassette containing the microarray.
6. Submerge the hybridization cassette in a water bath set at 62° C.
7. Hybridize for 6 hrs at 62° C.
8. Following hybridization, remove the microarray from the hybridization cassette and place it immediately into the wash station.
9. Wash the microarray for 5 mm at room temperature in 1×SSC+0.1% SDS.
10. Transfer the wash station and microarray to a second beaker containing 400 ml 0.1×SSC and 0.1% SDS.
11. Wash the microarray for 5 mm. at room temperature 0.1×SSC 10 and 0.1% SDS.
12. Rinse the microarray briefly in a third beaker containing 0.1×SSC to remove the SDS.
13. Allow the micro arrays to air dry.
14. Scan the microarray with the ScanArray 3000, 4000 or 5000 to collect fluorescent emission.
15. Quantitate the fluorescent emission at each position within the microarray.
16. Assign gene expression values of the detected biological entities by comparing the experimental data to the appropriate controls.

It should be noted that cover slips must be free of oils, dust and other contaminants. Lower the cover slip onto the microarray from left to right so that the sample pushes out air bubbles as it forms a monolayer against the microarray surface. Small air bubbles trapped under the cover slip exit after several minutes at 62° C.

In a preferred embodiment, a temperature of 62° C. works well for cDNA-cDNA hybridizations. Lower temperatures should be used for hybridization to oligonucleotides. c. Wash station should be placed in a 600 ml beaker containing 400 mL SSC+0.1% SDS. The microarray should be transferred quickly from the cassette to the wash station. Leaving the microarray at room temperature will lead to elevated background fluorescence.

In another preferred embodiment, the cover slip should slide off the microarray during the wash step. If the cover slip does not slide off within 30 sec, use forceps to gently remove it from the microarray surface. Failure to remove the cover slip will prevent efficient washing of the microarray.

2. Preparation of Labeled Nucleic Acid from a Sample
1. Prepare total nucleic acids from sample to be tested.
2. Amplify the nucleic acids by PCR using short random primers.
3. To a microfuge tube, add 71 microliter $H_2O$, 10 microliter 10×PCR buffer (500 mM KCl, 100 mM Tris-Cl pH 8.3, 15 mM MgCl2, 0.1% gelatin), 10 microliter dNTPs (2 mM each), 5 microliter Cy5-dCTP (1 mM)a, 2.0 microliter short random oligonucleotide primers (100 pmole/microliter), 1 microliter total nucleic acids from sample (0.5 microgram/microliter). Mix by tapping the microfuge tube gently.
4. Add 1.0 microliter Taq DNA polymerase (5 units/microliter). Mix by tapping the microfuge tube gently.
5. Generate fluorescent, single-stranded cDNAs by linear amplification of the total nucleic acids according to the following regime: [denature at 95° C. for 2 mm, amplify for cycles of (94° C. 30 sec. 55° C. 30 sec, 72° C. 30 sec), extend at 72° C. 3 mm, hold at 4° until ready to purify].
6. Purify the fluorescent linear amplification products on a QIAquick column.
7. Evaporate the purified products to dryness on a speedvac.
8. Resuspend the pellet in 50 microliter of 1×TE (10 mM Tris-Cl and 1 mM EDTA) pH 8.0.

3. Preparation of Labeled Control Nucleic Acids
Equipment and Reagents
Perkin Elmer 9600 Thermal Cycler (or equivalent)
QIAquick PCR purification kit (Qiagen #28106)
Method
1. Obtain a heterologous cDNA cloned into a plasmid vector.
2. Amplify the cDNA insert by PCR using cDNA-specific primers.
3. Purify the amplified cDNA insert using a QIAquick column.
4. Evaporate the sample to dryness in a speedvac.
5. Resuspend the purified cDNA insert in 10 microliter 1×TE (10 mM Tris-Cl and 1 mM EDTA) pH 8.0.
6. To a microfuge tube, add 71 microliter $H_2O$, 10 microliter 10×PCR buffer (500 mM KCl, 100 mM Tris-Cl pH 8.3, 15 mM MgC 12, 0.1% gelatin), 10 microliter dNTPs (2 mM each), 5 microliter Cy5-dCTP (1 mM)a, 2.0 microliter-mer oligonucleotide (100 pmole/microliter), 1 microliter cDNA PCR product (0.5 microgram/microliter). Mix by tapping the microfuge tube gently.
7. Add 1.0 microliter Taq DNA polymerase (5 units/microliter). Mix by tapping the microfuge tube gently.
8. Generate fluorescent, single-stranded cDNAs by linear amplification of the template according to the following regime: [denature at 95° C. for 2 mm, amplify for cycles of (94° C. 30 sec, 55° C. 30 sec, 72° C. 30 sec), extend at 72° C. 3 mm, hold at 4° until ready to purify].
9. Purify the fluorescent linear amplification products on a QIAquick column.
10. Evaporate the purified products to dryness on a speedvac.
11. Resuspend the pellet in 50 microliter of 1×TE (10 mM Tris-Cl and 1 mM EDTA) pH 8.0. The concentration of the fluorescent, single-stranded cDNA is preferably 40 ng/microliter.
12. Add 1.0 microliter of the 40 ng/microliter fluorescent control per microliter hybridization buffer to provide a fluorescent, single-stranded cDNA control at 2 ng/microliter.
    a. Alternate fluors such as F12-dUTP, L5-dCTP and Cy5-dCTP can also be used.
    b. Controls of this type provide a measure of hybridization and scanning, independent of an enzymatic labeling step such as reverse transcription. A 2 ng/microliter single-stranded product should produce an intense fluorescent signal equivalent to an abundant cellular transcript.

Multiple fluorescent cDNAs can be used to generate a concentration series.

Example 3

Analyses of a Sample Containing Multiple Biological Organisms

Three experiments were run with samples containing a mixture of biological entities, specifically *E. coli* and *Bacillus subtilis*. The mixtures were constructed such that the ratio of *E. coli* to *Bacillus subtilis* was 10:1:1, and 1:10, respectively. The results for the 1:1 mixture showed approximately equal signals for each genome, while the other two experiments showed heavier signals for the predominant organism, but continued to show signals for the less prevalent organism.

Example 4

An entire bacterial genome can be randomly amplified using the polymerase chain reaction (PCR) and this reaction will produce a sample that represents the entire DNA sequence of that bacteria. The reaction should include genomic DNA as a template, random primer that can range from 6 to 10 nucleotides in length, and other generic reagents (i.e., buffer, magnesium chloride, deoxynucleotide triphosphates (NIP), and a heat stable DNA polymerase) necessary for the success of PCR.

SUMMARY OF EXPERIMENTAL EVIDENCE

I. Experiment confirms there is a product produced by randomly amplifying genomic DNA with PCR.

II. Experiment proves that a biotin labeled specific segment of DNA will bind to randomly primed PCR products and accordingly give a hybridization signal.

III. A. and B. Experiments show that two bacterial species can be distinguished based on the sequence identity of a gene shared between the two species.

IV. Experiment demonstrates that random primed PCR products from two bacterial species can be used to identify DNA sequences from a specific species.

V. Experiment demonstrates that randomly amplifying an entire genome through PCR can produce a sample that is representative of the entire DNA sequence of that genome.

VI. Experiment demonstrates that the random, isothermal amplification techniques using the Klenow enzyme can successfully produce a product from *E. coli* that represents the entire *E. coli* genome.

VII. To help advance our technology into the microarray format, this experiment demonstrated which slide type, DNA concentration, and spotting buffer should be to used to achieve the best possible spotting morphology.

VIII. Experiment demonstrates that species specific hybridization can occur in the microarray format using fluorescent labeled probe.

I

Experimental Background and Purpose

Experiments were started to determine if random amplification of bacterial genomic DNA was possible through the polymerase chain reaction (PCR). To achieve this, PCR reactions were prepared that contained random octamers and random nanomers (separate reactions) as the primer component of the reaction. The initial template used was *E. coli* genomic DNA (12.5 nanogram per reaction). All other PCR components used were part of standard PCR protocols and at standard concentrations (final concentrations and total amounts per reaction are as follows: [PCR buffer w/o $MgCl_2$]= 1X, [$MgCl_2$]=2 mM, [$NTP_4$]=200 uM, Taq polymerase=1.25 units). The initial tests of these reactions included serial dilutions of the primers ranging from 500 ng to 4 ng per reaction.

The PCR program followed standard temperatures for denaturation of DNA and extension of the primer/Taq complex (94° C. and 72° C., respectively). To determine the annealing temperature for each primer, a temperature gradient was used ranging from 31° C. to 55° C.

Results

The PCR reaction was successful with the random octamers. These primers produced the expected product (a smear on an agarose gel) at concentrations of 500 and 100 ng and annealed at 31° C. for two minutes. The random nanomer also produced the expected product with 500 ng of primer at 31° C. and 34.8° C. annealing temperature for two minutes.

II

Experimental Background and Purpose

A series of hybridization experiments were conducted to show that biotin labeled probe of specific DNA sequence would hybridize with random primed PCR products from the same or similar bacteria. Random primed PCR products from *E. coli* were spotted on a membrane along with another gene specific PCR product from *E. coli* called 475. The membrane was hybridized with biotin labeled 475 PCR product. This experiment was repeated with higher stringency wash conditions. Also, a complimentary experiment was done using a similar blot hybridized with biotin labeled random primed DNA from *E. coli*.

Results

When probed with 475 DNA, the 475 spot showed a strong hybridization signal and the random primed DNA showed a light hybridization signal. The later experiment performed with high stringency washes showed a stronger signal for the random primed DNA and a light signal for the 475 DNA. When a similar blot was probed with random primed *E. coli* DNA (from the random octamers), the 475 produced a strong signal and the random primed DNA also produced a relatively strong signal. Overall, these experiments demonstrated that random primed PCR products could successfully be used in hybridization experiments for the detection of the specific 475 PCR product.

III

A. Experimental Background and Purpose

To validate the idea that different species of bacteria could be distinguished using PCR products, a hybridization experiment was conducted where gene specific PCR products known as 1360 from *E. coli* and *B. subtilis* were spotted onto duplicate membranes. One was probed with biotinylated 1360 generated from *B. subtilis* while one was probed with a biotinylated *E. coli* 1360 probe. Because the PCR products used in this experiment are not completely homologous in these two bacterial species, it was expected that the probe from *E. coli* would bind to both *E. coli* and *B. subtilis* targets, but it would show a greater affinity for the *E. coli* target. Likewise, the *B. subtilis* probe would bind to targets from both species, but show a stronger signal for the *B. subtilis* target. The experiment was carried out at low stringency temperature for the hybridization and washes (37° C. for both).

Results

The membrane hybridized with the *B. subtilis* 1360 probe showed a strong signal for *B. subtilis* 1360 as expected. This membrane also showed a light hybridization signal for *E. coli*

1360, *E. coli* 475 and *B. subtilis* 475. The membrane probed with *E. coli* 1360 probe showed a strong hybridization signal for *E. coli* 1360 and 475 and a lighter signal for *B. subtilis* 1360. These results were in agreement with the hypothesis declared above. Overall, these results indicate that when two species of bacteria express a similar gene(s), it is possible to distinguish these two species based on the degree of homology between the genes.

B. Experimental Background and Purpose

The purpose for this experiment was to reaffirm that two species of bacteria could be distinguished based on a gene that is shared between the two species. This experiment is similar to the one mentioned above and was conducted to show species specific hybridization. Basically, the PCR product known as 1360 was amplified from both *E. coli* and *B. globigii* in separate reactions. The 1360 DNA from both species was then blotted on duplicate membranes. One membrane was probed with biotinylated *E. coli* 1360 DNA and one was probed with biotinylated *B. globigii* 1360 DNA. It was expected that the *E. coli* probe would bind strongly to itself but still show a slight signal for the *B. globigii* 1360 DNA and vice versa for the *B. globigii* probe.

Results

The results clearly support the hypothesis of this experiment. The blot probed with biotinylated *E. coli* 1360 shows a strong signal for two *E. coli* 1360 spots (one at 20 nglul and one at 4 ng/ul) and shows a very light signal for the *B. globigii* 1360 DNA. The blot probed with *B. globigii* 1360 DNA shows a strong signal for the *B. globigii* 1360 DNA and a light signal for the *E. coli* 1360 DNA. These signals suggest that it is possible to show species specific hybridization with similar segments of DNA from the bacterial species in question.

IV

Experimental Background and Purpose

This experiment was conducted to determine if random primed PCR products from two bacterial species could be used to identify species specific DNA sequences. DNA sequences shared between *E. coli* and *B. subtilis* were blotted to a membrane along with DNA sequences that are unique to each bacterial species. This membrane was then probed with randomly primed (via a random octamer) *E. coli* genomic DNA amplified by PCR.

Results

The randomly primed *E. coli* probe showed a signal for the following DNA targets: *E. coli* 475, *B. globigii* 475, *E. coli* 1360, *B. globigii* 1360, *E. coli* "citrate" DNA (light signal), random primed *E. coli* DNA. The unique DNA from *B. globigii* did not show a signal and the random primed *B. globigii* DNA showed a very faint signal. These results indicate that it is possible to show species specific hybridization using randomly primed PCR as the technique to amplify an entire bacterial genome.

V

Experimental Background and Purpose

To further emphasize that random priming an entire genome by PCR (RP PCR) can produce a representative array from that specific genome, a hybridization experiment was conducted using lambda phage genomic DNA as the target and randomly primed lambda DNA as the probe. First, biotinylated lambda genomic DNA was generated using an isothermal reaction in which a small subunit of DNA polymerase I (Klenow enzyme) was used to amplify the entire genome. This probe was previously shown to completely represent the lambda genome and was used as a positive control. Another biotinylated lambda probe was generated using the standard RP PCR protocol.

To compare the RP PCR probe with the "Klenow" probe, a southern blot was produced with lambda DNA previously digested with two restriction enzymes. Duplicate strips from this blot were then probed with the two lambda probes mentioned above.

Results

The results of the hybridization show that the RP PCR probe does represent the entire genome and is comparable to the probe prepared by the Klenow method. The Klenow probe produced a signal for every band of the lambda DNA, as did the RP PCR probe. The results of this experiment further supports the proposal that randomly priming an entire genome through PCR can produce a sample that is a database for the entire DNA sequence of that genome.

VI

Experimental Background and Purpose

This experiment was conducted to determine if the Klenow amplification used in the above experiment (V.) could successfully produce a sample that is representative of a more complex genome such as the bacterial genome of *E. coli*. First, the Klenow reaction was carried out with *E. coli* genomic DNA (previously digested by restriction enzyme HinfI) as template and a biotin dNTP as the label. This probe was then used in a hybridization experiment with a Southern blot containing *E. coli* genomic DNA that had been previously digested by a restriction enzyme. Also, this probe was used in another hybridization with a dot blot containing *E. coli* genomic DNA, several specific DNA sequences unique to *E. coli* and several sequences unique to *Bacillus subtilis*, and several specific sequences that are shared between the two bacteria.

Results

The results of the dot blot hybridization showed a very strong signal for the *E. coli* genomic DNA target. The probe also produced signals for the unique *E. coli* DNA targets and the targets shared between *E. coli* and *B. subtilis*. For the targets that are shared between the two species, there was a stronger signal for the *E. coli* target than for the *B. subtilis* target. There was not a signal for the DNA sequences that were unique to *B. subtilis*.

The results of the Southern blot hybridization revealed a smeared signal the entire length of the blot, corresponding to the smear of *E. coli* genomic DNA on the gel. These results indicate that the product of the isothermal Klenow amplification reaction can be used with larger bacterial genomes to successfully generate a representative sample of the *E. coli* genome. Furthermore, as seen with the dot blot hybridization, this product can be sued to distinguish between two bacterial species.

VII

Experimental Background and Purpose

To help advance our technology into the microarray format, experiments were begun to determine optimal DNA concentration, spotting buffer and slide type for future microarray experiments. Lambda phage DNA was used in 2 fold serial dilutions starting at 500 ng/ul and mixed with one of three spotting buffers: 3×SSC, 3×SSC plus 0.1% sarkosyl, and 1×SSC plus 0.1% sarkosyl. Two slide types were used in this experiment: poly-1-lysine coated slides and amino-silane coated slides.

The lambda dilutions in each of the three buffers were spotted on the two slide types using the Affymetrix 417 Microarrayer. The Applied Precision Array Works Microarray Scanner analyzed the slides.

Results

The amino-silane slides had well defined spots, while the poly-1-lysine slides had overall poor spot morphology and smearing. The samples with higher DNA concentrations (500 ng/ul and 250 ng/ul) showed the best spot morphology when combined with the 3×SSC plus 0.1% sarkosyl spotting buffer. Conclusions were made to continue to use the amino-silane coated slides with 250 ng/ul final DNA concentration in 3×SSC plus 0.1% sarkosyl.

VIII

Experimental Background and Purpose

To demonstrate that species specific DNA segments could be distinguished in microarray format, a series of PCR products containing open reading frames (ORFs) from E. coli and B. subtilis were printed on microarray slides. Several of these slides were then hybridized with a fluorescent probe generated from E. coli genomic DNA randomly amplified by the Klenow method.

Results

The fluorescent E. coli probe produced signals from the E. coli ORFs but did not produce any signal from the B. subtilis ORFs. This indicates that species specific hybridization can be detected in microarray format using fluoroscently labeled probes.

Preliminary analysis of the results from the hybridization of slide 296359 with two Klenow probes (4 & 5) which correspond to E. coli and B. sub indicates some targets are recognized as more similar to E. coli and others are more similar to B. sub. There are also indications that targets too close to the edge of the slide or edge of the coverslip do not provide a reliable signal.

An experiment was begun to stain two slides with SYBR Green II, scan and record the data, then destain these slides to include them in a subsequent Hybridization experiment using duel color/duel species PCR derived probes. The staining resulted in an intense signal which was mostly removed by the destaining procedure. These two slides were later used in another hybridization experiment.

A hybridization with slides 296364-296367 to observe the hybridization signal from a single probe (19) derived from Cy 3 PCR labeling of E. coli template and purified for either 2, 3, 4 or 5 passes through a YM3O microcon chamber was performed. The result was that except for slide 296366, a progressive loss in background was observed in general with increasing purification.

Slide 296366 was hybridized with probe 19 after five passes of purification. This slide showed a very high background and a very bizarre signal pattern. Most of the target spots had spread out considerably and there was a signal obtained from targets that none of the other three slides in this series showed, for example from Micrococcal luteus target spots. Disregarding this slide, the trend was good and the slide hybridized with probe 19 purified 4 times had the best signal and lowest background.

An experiment was performed with slides 296360-296363. The slide pair 296360 and 296361, was hybridized using probes 21 and 30 which are Cy3 E. coli and Cy5 B. sub respectively. The slide pair 296362 and 296363, was hybridized using probes 24 and 27 which are Cy5 E. coli and Cy3 B. sub respectively. This experiment worked well enough to show that we can distinguish one species from another by this hybridization. This is equivalent to the results obtained on September 10 of this same week using Klenow derived probes, except that the background signal was a bit higher.

In summary, with the hybridization experiments made a fundamental demonstration that the approach of using random-primed PCR-labeled probes to determine the identity of the bacterial species used to make the PCR product does work, based on the resulting pattern of hybridization on the microarray.

An experiment using a streptavidin linked Alexa fluor 647 dye to detect hybridization with biotinylated probe was performed. Also, began another SYBR Green II staining experiment using slide 296341. Our previous experiment like this had worked well but the signal was a little patchy. We had been able to destain pretty well and subsequently hybridize that earlier slide.

Also, made a total of fifteen new slides, 296356 through 296370. These slides contain both positive and negative controls such as: E. coli, B. sub, M. luteus, B. pertussis, C. perfringens, and Herring sperm genomic DNA. They also included the newly made ORF PCR products from B. sub.

A hybridization of slide 296356 with Cy 3 PCR E. coli probe (#17) and slide 296357 with Cy3 PCR B. sub probe (#18) was performed. This experiment resulted in very high specific activity at the lower nucleotide concentrations. Hybridization was overnight at 55 deg. Scanned both images on September 4. They both have a great deal of background but they also have a high level of signal.

An experiment duplicating the previous experiment but with further purification of the PCR probes was performed. Purified probe 16, (E. coli, PCR, Cy3) 2 more times and then hybridized slide 296358 with it for 2 hours at 67 deg. Scanning the slide showed very strong and consistent hybridization with still a bit of background.

In control experiments, slide 296343 was hybridized overnight with Klenow labeled alexa488 probe and slide 296344 overnight with Cy5 labeled probe. These probes yielded a good signal with good descrimination between E. coli and B. glob targets. The data was very tight compared to earlier hybridizations. The Klenow probes are our best standard of performance.

Began development of a protocol for short (two hour) hybridization that still shows discrimination between coli and glob target spots. Slides 296343 and 296344 were hybridized with alexa488 probe except that 296343 was at 52 deg and 296344 was at 65 deg. The 52 deg hybridization had a good signal but no discrimination. The 65 deg hybridization showed a good signal and good discrimination of target spots. At 65 deg hybridization there was also a marked reduction in hybridization to herring sperm DNA control spots, which is good.

Hybridized the SYBR Green II stripped slide (296330) as well as 296351 with Cy5 E. coli and Cy3 B. glob. The 296330 slide was hybridized for 2 hours @67 deg, the 296351 slide was hybridized overnight @52 deg. The 296330 slide showed good distinction of one species from another with almost no SYBR Green II signal left.

Summary of Early Microarray Results

Random primed probe derived from E. coli can distinguish the E. coli target spots from B. glob spots when hybridization is carried out for sufficient time and the probe is in sufficient mass and specific activity. PCR and Klenow derived probes can discriminate between E. coli and B. glob spots when hybridization is carried out overnight. Shorter hybridizations seem to demonstrate a short-term signal from the inappropriate target spots that later is lost. This suggests complex kinetics of association/disassociation and target excess. Target excess is also suggested when high levels of probe were applied and which resulted in increased signal. The Klenow derived probes are a standard for hybridization because of their greater availability. It is possible to estimate relative specific activity by measuring the ratio of fluor absorbance to DNA absorbance. SYBR Green II staining provides a useful measure of target DNA mass and thus may serve as an internal control to refine our protocol.

Example 5

There currently exists a technology void in the area of rapid, multi-dimensional characterization of biological species in a given environment. The wide diversity of microorganisms requires that a technology be developed that can definitively identify and characterize hundreds of biological species within a short time period at a reasonable cost. This capability is necessary if we are to rapidly detect and identify perturbations in the normal flora or in the introduction of organisms not typically found in a particular environment. Our goal is to develop a pattern recognition capability to characterize a biological sample.

Current methods used to identify biological species include antibody-based systems, specific nucleic acid identification, or microbiological analysis. These systems are severely limited in "throughput". The specificity and sensitivity of particular antibodies or antibody mixes must be determined empirically. Nucleic acid-based assays typically only target one species per tube. Microbiological analysis can provide a broad characterization of organisms in a sample, but might miss unexpected species. In addition, the cost and the time requirements for this extensive analysis is prohibitive. Costs for extensive characterization (greater than ten organisms) can cost well in excess of $10,000 per sample.

We propose to employ a new technological approach for the detection and identification of hundreds to thousands of specific DNA sequences within a single sample. This represents a significant enhancement over current protocols. Our random primer PCR/DNA chip identification approach can be used for identification of bacteria and/or viruses in the environment. In addition, our approach to characterization of environmental samples leverages the substantial investments from both government and industry for the identification and characterization of diverse environmental samples. This proprietary technology combines the polymerase chain reaction (PCR) mechanism of DNA replication and amplification and the more recently developed gene chip, or microarray, technologies.

Our unique combination of these two disciplines will allow one to ask hundreds to thousands of questions regarding the nucleic acid content of environmental samples. This approach may enable us to characterize complex mixtures of biological organisms in 60 minutes or less.

The technologies of PCR and DNA microarrays are well established in the medical diagnostic industry. A key strength of our proposed proprietary system is the ability to answer hundreds of broad as well as specific questions about the DNA in a sample in a single assay format. This allows us to employ a phylogenetic approach to identification, thereby dramatically improving our identification capabilities. This should enable us to perform broad background characterizations, to detect novel genetically engineered species, and to provide partial answers to identify unknown organisms related to a particular class of virus or bacteria as determined by the phylogenetic pattern. This is critical in the case of unknown or unexpected pathogens or when biological agents are suspected of being present in the environment. Current technological approaches are directed at a limited number of organisms suspected of being attractive as BW agents. Our technology should identify these agents as well as many others.

Current identification systems can only identify a very limited number of organisms in near-real time. Our novel approach will enable us to positively identify hundreds of pathogens in minutes to hours using a single microarray, or DNA chip. Moreover, by producing a hierarchical array of DNA fragments, some of which are highly conserved among species and others which are unique to particular species or strains of pathogens, our system will provide partial identification or background characterization. In short, this proprietary system can provide a detailed characterization of environmental samples in minutes that can currently only be achieved in the laboratory in days to weeks. The benefit of our identification system is a dramatic improvement in multiplexed characterization, a critical element for understanding the occurrence and nature of a biological perturbation of the environment.

BACKGROUND

Current biological detection and identification systems rely on two prominent technologies, antibody recognition and PCR amplification and identification. Mass spectrometer systems have also been making significant progress, but have not overcome the significant challenges of complex backgrounds. There is a pressing need for increases in capability of our ability to identify organisms in a complex sample. Scientific advances, as well as changes in our global travel patterns, have enabled introduction of previously uncharacterized organisms into new populations. There is a need for systems to address current as well as future threats.

Conventional structure based systems such as antibody binding and sequence specific PCR amplification reactions are effective identification methods. However, they are limited in their ability to ask large numbers of questions simultaneously. Antibody systems also target a limited number of organisms and epitopes (generally protein components) specific for a particular organism. Antibody detection of organisms is hindered by lack of sensitivity and specificity, but does not require nucleic acid signatures for identification. This ability makes the technology attractive for the identification of biological toxins. DNA-based detection systems, such as the system presented here, may be able to detect the presence of toxins if the preparation is contaminated with DNA fragments from the host organism.

PCR based systems use specific primers and probes to ask very specific questions about the target organisms. PCR is a licensed technology for the amplification of DNA. Generally this technique is used to amplify one or two specific regions of DNA from a target organism for later analysis. Used in this manner, our proprietary system can detect a single copy of DNA among billions of other segments of DNA. The specificity is determined by the nucleic acid sequence of the primers, or starting templates, for amplification. These primers are usually on the order of 20-25 nucleic acids in length. The longer the length, the greater the specificity. This standard application of PCR technology provides substantial sensitivity and selectivity. A limitation of conventional approaches is that generally only one organism is targeted per reaction tube.

Another method for the amplification of DNA within a given sample is the use of "random primers." Random primers are much shorter in length. This short size results in hybridization at multiple locations such that practically all the DNA in a given is amplified. The primers anneal to many places in the genome, hence the nomenclature "random", but the fidelity of the amplification is equal to that of other PCR methods and the amplified sequences are identical to sequences present in the original sample. The size of the amplified fragments can be adjusted by using various levels of primers and by varying the number of amplification reactions. In theory, the greater the number of amplifications, and the higher the level of primers, the greater the proportion of shorter amplified regions of DNA.

DNA arrays are constructed by two distinct technologies. The result is a gridded array of thousands of specific DNA sequences immobilized on either glass or opaque membrane within a square centimeter. Affymetrix patented technology synthesizes the DNA chain directly linked to the glass slide. Laws of physics prevent them from constructing arrays with many more than 25 bases in length. The other approach is to spot small volumes of a solution containing DNA onto the slide or membrane. The DNA is then immobilized and denatured to allow subsequent hybridization with amplified labeled DNA fragments. Using these technologies, investigators have patterned thousands of DNA sequences representing thousands of genes on single chips. The preponderance of literature and patents are on the use of these gene chips to identify gene regulation as a function of external stress or disease condition. Thus far the integration of PCR with gene chip technology involves either amplification of specific regions of DNA, or synthesizing complimentary DNA to messenger RNA within a cell as an indicator of gene activity. The gene chips are then used to determine the expression patterns.

We are developing a prototype microarray, or DNA chip, on membranes and glass for the identification of multiple biological species in environmental samples. Our approach will allow us to detect, in a single assay system, what currently requires hundreds of individual assays. Our proposed system will be composed of one reaction tube in which we will amplify and incorporate a molecular tag into essentially all DNA in an environmental sample. The amplified/tagged DNA will then be exposed to a microarray, or DNA chip, containing hundreds of DNA fragments that can answer broad, as well as specific, questions about the identity of the DNA present in the sample. This chip represents our proprietary phylogenic approach to species identification. Matching DNA fragments from the amplified sample will be captured (hybridize) on specific areas of the DNA chip and an optical signal from the molecular tag incorporated into the amplified DNA will be detected. Off-the shelf hardware and software will be used to read and interpret the pattern of spots that identify what organisms are present in the sample. This system will provide the capability to identify up to hundreds of species from a single sample within a target window of 60 minutes.

Due to the fact that we label and amplify in a random fashion, all segments of the genome should be represented. This will allow us to look for hundreds to thousands of genetic sequences. These genetic elements will include conserved as well as unique sequences. In addition, we can look for presence or absence of sequences that are suggestive or indicative of genetic manipulations. Variations in hybridization stringency may also provide key information when screening for nearest neighbors related to organisms of interest.

We will take a hierarchical (phylogenic) approach to agent identification. We plan to spot DNA chips with known DNA sequences. We will have regions of the chip containing highly conserved regions of DNA, as well as unique regions. For example, *Bacillus anthracis* DNA would hybridize to a generic bacterial DNA spot, it would not hybridize to a human specific region, or a virus specific region. This amplified DNA would also bind to a *Bacillus* specific region, but not to a unique Bacillis globigii sequence. It would bind to regions specific for *Bacillus anthracis*. The requirement for multiple positive hybridization regions will decrease the probability of false positive readings.

Our array will also be constructed to provide broad as well as specific identification. For example, 16S ribosomal DNA will be used to establish the presence of bacteria, conserved *bacillus* sequences will be used to identify all *bacillus* species presence, and specific DNA will further classify the *bacillus* species or strain. All of these hybridizations should be positive if the target organism is present in the sample. Identification of target sequences is a key element for the success of this proprietary phylogenic analysis system. Many appropriate sequences already exist within the public domain, or have been generated by Government funding. Use of these sequences as proposed herein, however is regarded as unique. These systems are capable of containing these of thousands of sequences on a single chip. We believe that a redundant approach for each organism will provide the best method for the characterization of unknown species, or species with introductions of foreign DNA.

This identification system will be designed to be incorporated into an existing DNA amplification system. This approach will expedite the development of a complete system for laboratory and field systems.

This system will employ random PCR amplification and microarray technologies, in concert with a DNA amplification system, as the principle system component for our analytical module in order to identify biological species present in a sample. This system will employ random primer PCR with a phylogenic discrimination approach on a DNA based microarray, and as such, will not be constrained by the number of biological entities in the sample. This system shall also have the capability of providing initial characterization of unknown entities based upon the phylogenetic hierarchical array of the DNA chip in that we would provide partial characterization with our phylogenic approach. In addition, the association of functional elements of one pathogenic organism in the absence of its associated structural elements will provide significant evidence of genetic manipulation of that organism for structural as well as virulence genes from target species. The presence of virulence genes, in the absence of structural genes, is an indication that these virulence genes have been inserted into another organism. Agents to be considered over this three year period will include bacteria and viruses on the DOD threat list and widely recognized simulants of those agents.

Example 6

We propose to develop a procedure to identify biological species within a given sample. This sample may be a forensic or a medical specimen. This unique process will be based on genetic information contained within the respective genomes of biological organisms. The genetic structure of an organism is the most consistent structural basis for identification. Both protein and lipid content of biological organisms can be altered as a function of growth cycle and growth nutrients. The DNA structure and sequence are unaltered by growth or culture conditions. Our procedure will first conduct three key procedures in parallel using the DNA present in the sample as a template. We will amplify the amount of DNA, which will improve sensitivity. We will fragment all of the genomes present in the sample because entire genomes are far too complex for rapid analysis. Finally, we will incorporate a label, or tag into the fragmented genome. This tag provides the basis of identification. All three of these reactions combine to generate a fragmented, labeled representation of all genomes present in the starting material. This material will then be analyzed using DNA array technology to identify the presence of characteristic sequences from specific organisms. The pattern of spots hybridizing will be representative of the genomes present in the original sample. Multiple sequences for each organism can be arrayed to add redundancy and stringency. Because of the conserved nature of DNA sequences, this technique will provide partial characterization of unknown organisms. In addition this approach can also provide key indicators of genetic manipulations resulting in chimeric organisms. Specific details regarding the proprietary approaches are contained within this proposal.

Example 7

Novel Pathogen Identification Technology Using DNA Amplification and Microarray

PROBLEM: The threat of the use of biological weapons (BW) against US civilians is believed to be steadily increasing. Attacks on US soil have been apparently limited to a food poisoning attack by the Bhagwah Shee Rajneesh. However, there have been numerous documented unsuccessful BW attacks in Japan by the Aum Shinrikyo cult. The fact that this organization employed a non-virulent vaccine strain of *Bacillus anthracis* resulted in little more than citizen's complaints of foul odors. Had the released bacterial spores been an infectious form of the organism, the results could have been catastrophic. These two separate occurrences demonstrate the vulnerability of our society to an offensive BW attack. Our medical and responder communities are not prepared for such an emergency. Our medical infrastructure is not prepared to treat large numbers of casualties, and our medical diagnostic system is not adequately trained to diagnose for many of the diseases considered most likely in an attack. This situation is exacerbated by the fact that many of the diseases that are considered prime candidates for BW use are not responsive to conventional therapy once symptoms develop. This single sobering fact makes the diagnosis and treatment of these diseases extremely difficult. A publication by Kauffmann at the Centers for Disease Control concluded "Rapid implementation of a post attack prophylaxis program is the single most important means of reducing these losses." The "losses" referred to are both economic and human lives. This scenario-based study identified the capability to correctly identify the biological characteristics of a given sample of paramount importance in order that appropriate therapies could be administered within the therapeutic window. However, despite significant increases in funding for biomedical research, both in the areas of diagnostics and treatment, we are still unprepared for an offensive attack.

Identification and characterization of biological agents is critical to the medical and forensic communities. Accurate and rapid identifications aid treatment and law enforcement alike. Standard microbiological techniques are effective for characterization of biological organisms, but generally take days before results are finalized. Antibody based identifications are more rapid, but are limited to organisms against which we have sensitive and specific antibodies. Each antibody is designed to ask a single question, "Is the target organism present at concentrations above the limit of detection for the system?" These questions can either be asked in series or in parallel, depending on the configuration of the system. In addition, these assays frequently can not distinguish between infectious and vaccine strains of organisms and therefore have limited forensic value. Standard polymerase chain reaction (PCR) based nucleic acid based identification techniques are sensitive and specific, but are limited in their complexity, generally designed to identify the presence of a single, pre-characterized organism. The polymerase chain reaction (PCR) is a technique to specifically amplify known regions of DNA by repeated cycles of a chemical reaction that copies a segment of DNA from a template strand. Specific DNA primers that are generally 20-25 bases in length identify the ends of the unique sequence. Primer length and sequence determine the specificity of binding to template (unknown DNA), and therefore the subsequent DNA amplification. Although these systems are highly sensitive and specific, they generally look for the presence of one bacterial species at a time. Multiple reactions must be conducted in order to identify multiple bacteria. Although currently "state-of-the-art," the above approaches have limitations. Specific reagents (antibodies or nucleic acid primer and probe sequences) are developed to detect each pathogen of interest. Thus, these systems provide only a yes/no answer for each pathogen for which a test has been developed. They are not configured to characterize complex biological samples, unexpected or previously uncharacterized organisms, or those subjected to genetic manipulation. Assuming tests for organisms present in a sample are included, a potential pitfall of this approach is that one may stop testing after the first positive reaction, when the sample may contain multiple pathogens. There exists a technology void in the area of rapid, multi-dimensional characterization of biological species in a given environment. The wide diversity of microorganisms requires that a technology be developed that can definitively identify and characterize hundreds of biological species within a short time period at a reasonable cost. This capability is necessary if we are to rapidly detect and identify perturbations in the normal flora or in the introduction of organisms not typically found in a particular environment. Our goal is to develop such a technology to rapidly characterize a biological sample based on the DNA present.

Goals

The goals of this effort are to develop and demonstrate integration of two distinct molecular biological technologies for rapid characterization and identification of biological organisms. If successful, we will be able to identify the presence of single or multiple organisms within a given sample within hours. This technical approach looks for the presence of known DNA sequences for a massively parallel characterization of a sample. The first technology involves DNA amplification, fragmentation and labeling, the second employs DNA microarray analysis. The proprietary approach to integrate these two technologies will offer a significantly enhanced capability over current methods to detect and identify bacterial biological agents in a sample of unknown composition. The DNA amplification will use a complex of random primers and conjugated nucleotides to amplify, fragment and label all DNA present in a sample. This approach is different than conventional nucleic acid amplification technologies, as a more complete representation of the genetic material in the sample is generated in a nonspecific manner. Standard nucleic acid amplification techniques, such as PCR, target a specific known sequence for amplification. Once all of the genetic information from a specific sample is fragmented and labeled, characterization of the amplified genetic material will be carried out through the use of DNA microarray technology.

DNA microarrays ("gene chips") are a newly established and accepted tool by which to measure the presence, expression level, and identity of genetic material (DNA or RNA) from an organism. They are widely used in the pharmaceutical industry to measure the expression profiles of thousands of genes simultaneously in response to drug treatment, or exposure to toxic compounds. Thousands of nucleic acid fragments, each specific for a gene or signature sequence, are bound covalently to a substrate (usually a glass slide). DNA or RNA from treated and untreated cells, or from cells from individuals with different medical histories, is labeled with fluorescent tags (different wavelength for control and experimental samples) are allowed to hybridize to the nucleic acids on the array. The identity of DNA or RNA species present in the sample and their quantity are determined by observing which of the chip-bound DNA spots have hybridized to labeled sample DNA or RNA. This approach is designed to identify regulation of gene expression of a single organism under different environmental conditions. Although we will take advantage of many of the scientific advances generated by this technology, we propose to take a fundamentally different approach to exploiting the massively parallel capabilities of this technology.

We will identify, generate and array DNA sequences that represent branch points in the phylogenetic tree. For example, we will array some DNA sequences that are conserved in all living things, some that are conserved in bacteria, some that are conserved in Gram positive bacteria, etc. until we travel from the trunk of the phylogenetic tree out smaller and higher branches to the twigs and leaves that represent DNA sequences that are specific to a strain or biovar of a particular bacteria. This approach exploits the plethora of DNA sequence information generated to date, and provides a template for incorporation of future data.

TECHNICAL APPROACH: We propose to develop an alternate approach to identification and characterization of biological species in a sample that will overcome the shortcomings listed above. As mentioned previously, PCR is generally used to amplify and identify very specific DNA sequences. However, DNA amplification technologies can also be used to amplify all DNA in a sample, regardless of the number of organisms present. We will use short "random primers" to initiate synthesis of new strands of DNA from many regions of the template DNA strand. In this way, we will fragment, copy and label genetic elements that essentially represent the entire genome of biological species present in the sample for subsequent characterization.

DNA microarray or "gene chip" technology is a method to detect the presence of nucleic acid sequences in a sample. Thousands of nucleic acid fragments, each specific for a gene or signature nucleic acid sequence, are arrayed in an addressable pattern on a substrate such as glass or a nylon membrane. We will use this technology to identify and characterize biological species in a sample by incubating the sample containing sequences generated using random amplification with specific DNA sequences on the array. Sequences on the array will be chosen to represent a phylogenetic array. Amplified sequences will hybridize with complementary sequences on the tree. Subsequent incubation with an avadin-linked enzyme and a substrate that forms a colored precipitate will allow us to capture a digitized image of the hybridization pattern that can be interpreted using computer software to characterize the biological species present in the sample.

Pathogens will be identified by the presence of multiple genetic sequences that identify each pathogen by genus, species, and strain. DNA sequences common to "all bacteria" and/or "all viruses" will be included as positive controls, and sequences from organisms in other phyla will serve as internal negative controls. Triplicate DNA "spots" designed into the microarray will provide replicates of each experiment on the chip for additional quality control.

Data generated demonstrate that we can perform random primer PCR on genomic DNA and produce biotin-labeled segments of DNA. These segments of DNA will hybridize to immobilized genomic DNA and are visualized by an enzymatic reporter system. Our expectations of the overall project are to be able to identify tens to hundreds of bacterial species from a single sample, thereby making greater than an order of magnitude improvement over existing systems. This capability will improve our counter terrorism capability to rapidly detect the presence of biological agents disseminated in a terrorist BW attack. This will enable faster, more effective treatment as well as a forensic capability to screen for a broad range of organisms to assist identification of perpetrators, prosecution and retribution.

We have demonstrated the incorporation of a biotin labeled nucleotide into standard PCR amplified regions of DNA using primer pairs of DNA. The incorporation of biotin does not interfere with subsequent hybridization reactions. Hybridizations were visualized following incubation with a streptavadin conjugated peroxidase enzyme. The avadin:enzyme conjugate binds to the biotin, thereby immobilizing the enzyme in the location of the biotinylated DNA strand. Addition of substrate for the enzyme results in a dark color developing wherever the enzyme is present indicating the location of the biotinylated DNA.

Using a DNA polymerase and random DNA primers, eight bases in length, we have generated DNA fragments from an *E. coli* template incorporating a biotinylated nucleotide. This biotin containing mixture of DNA sequences serves as our probe. We have purchased primer pairs for numerous DNA regions for the bacteria *Eschrecia coli* and *Bacillus subtilis*.

Using these primers, we have synthesized and purified these DNA sequences representative of the host organisms for MviM (*E. coli* ORF, Era (*E. coli* ORF), Ftn (*E. coli* ORF), Jag (*B. subtilis* ORF), Ruva (*B. subtilis* ORF), *E. coli* genoic DNA, *B. subtilis* genomic DNA, Herring Sperm DNA.

DNA Amplification. Standard DNA amplification chemistry is will be used. Short random primers will hybridize along the entire length of template DNA strands at multiple locations such that practically all the DNA present in a sample is amplified. Biotin labeled nucleotides will be incorporated during the amplification reactions to generate labeled DNA fragments. We will adjust reaction conditions and number of amplification cycles to produce fragments that are representative of the genome of organisms present.

Identify Bacterial Signature and Conserved DNA Sequences. Initial development efforts will focus on distinguishing a gram negative bacteria, *E. coli*, and gram positive bacteria, *B. globigii*. The genomes for both these organisms are in the open literature, which will facilitate selection of conserved and unique sequences to array on a gene chip. Conserved and unique sequences will be selected from the literature and tested to ensure that they hybridize to one or both of the test organisms Validated sequences will be applied to glass microarrays using our in-house Affymetrix 417 arrayer and optimized as described below.

Optimize DNA Chip Fabrication. An arrayer (e.g., Affymetrix 417) is used to spot designated DNA sequences onto glass-backed membranes. Once optimized, the gene chip spotting process is rapid. For example, 42 chips with 250 genes (25 organisms with 10 genes or signature sequences/organism) per chip can be produced in less than 3 hours.

Optimize chip hybridization and detection. An amplified, biotin-labeled sample of total DNA will be incubated with a gene chip prepared as described above and read with our Applied Precision Instruments microarray imager. Gene chip data will be analyzed using image analysis software package supplied by the manufacturer. The labeling conditions for the DNA, concentrations of labeled DNA, chip hybridization and washing conditions will be optimized to produce the most accurate strain ID data with the highest signal, in the least amount of time.

Add three additional organisms to system. Sequences to be arrayed to fully characterize three additional bacterial organisms for using this system can be determined. We will identify conserved and unique sequences, generate those sequences using standard PCR technology, and spot the sequences on the membrane array.

Improve Year 1 Bacterial Signature Sequences. In the second year, we will continue to add and delete genes/signature sequences from the array as more information becomes available on more species of threat agents. The system will be optimized to fully characterize organisms of interest, but will also provide partial characterization of related organisms.

Next, COTS CCD camera interface and analysis software are developed.

Optimize Hybridization Time and Affinity. We will continue to optimize hybridization conditions to increase to increase the speed and fidelity of our DNA characterization system. To do this, we will investigate oligonucleotide-based arrays and/or the use of synthetic peptide nucleic acids (PNA's) as the gene target material.

Improve Gene Chip Content and design. We will refine the phylogenetic hierarchical deign of the gene chip as more sequence data becomes more available in the public domain.

Incorporate chip with COTS CCD Camera Interface. We will incorporate the microarray slides with a commercially available CCD camera for imaging and analysis.

Example 8

We are developing a novel, scalable DNA amplification and hybridization-based biocomputing technology that that can quickly execute highly parallel Monte Carlo searches to solve computationally difficult problems. This approach utilizes a random primer generated complex information set of labeled DNA fragments, followed by computational analysis by a high-density immobilized DNA array. This novel computing technology involves the integration of four distinct technologies. Our team shall consist of a diverse collection of biochemists, molecular biologists, computer scientists and mathematicians.

The first innovation is a method by which we will generate a solution set consisting of a complex mixture of random-primed labeled DNA fragments. DNA fragments will be synthesized from genomic bacterial DNA using short random primers and the polymerase chain reaction (PCR) incorporating a fluorescent tag. The use of short primers present in excess, arid not as ordered pairs, produces labeled DNA fragments of various sizes. This product is a fragmented representation of all the information present in the genome.

A second innovation is the use of a high density DNA microarray that will serve as a content-addressable wet database of information objects that will be used to perform computational analysis of the random-primed DNA fragments comprising the solution set. The micro array will contain specific known DNA sequences to identify correct answers from the random-primed DNA solution set. The array will contain up to tens of thousands of spots, each containing many copies of a particular known DNA sequence. The DNA in a particular spot will hybridize only with fragments in the amplified, labeled mix that share sequence identity. The interaction of DNA fragments in the labeled solution set with the immobilized, known DNA sequences on the microarray is random, but the binding of fragments in the solution set to fragments on the array is very specific. This interaction forms the basis of a highly parallel molecular computation.

A third innovation is the content and configuration of specific DNA sequences, or information objects, contained in our wet database array. DNA sequences immobilized on the array will form a logic tree. Each spot will represent a branch point in the phylogenetic tree that will be used to identify biological species present in a sample. Analysis of the pattern of hybridization to the phylogenetic array will isolate outcomes that can be visualized and analyzed using digital computing techniques.

A fourth element of our approach is the integration of a digital computer to employ pattern recognition algorithms to assist in read-out and analysis of the hybridization pattern identified by the DNA chip. We will employ two approaches: neural nets and/or Bayesian inference nets. In biocomputing demonstrations to date, the optimal solution is encoded in the sample somewhat simplistically. For example, Adleman used DNA chain length to determine potential solutions from the biochemical reaction. We intend to encode the potential solutions on the gene chip in a more sophisticated manner and then use the pattern recognition capabilities of neural nets or Bayesian inference nets to extract and validate potential solutions.

The goal of this effort is to develop biochemical methods to perform complex computational analysis using solution-based and immobilized DNA fragments. We will use proprietary random-primed PCR as a scalable method for producing DNA fragments representative of the genome of biological species in a sample. We will combine this with a proprietary approach that arrays known sequences using a microarray format to serve as a scalable, high-density, content-addressable wet database. The combination of these two methods provides a massively parallel approach to solving complex computational problems.

An advantage of DNA-based computing approaches is that they can process information in a massively parallel manner. In contrast, conventional computers only analyze one potential answer at a time. Thus, problems that have many possible answers take a long time to solve, even for powerful computers that contain hundreds of electronic processors operating in parallel. This potential ability of DNA-based computing to operate in a massively parallel fashion allows for the prospect of scaling problem sets to levels that will eclipse the performance of conventional computers. Key innovations toward this goal involve encoding a mathematical problem in a format such that biochemical reactions can be used to quickly generate a large potential solution set and to extract correct answers from the possible solutions.

We propose to use our technology combining random primer PCR and a phylogenetic DNA chip to create a large solution set quickly, and extract appropriate solutions as a pattern of DNA fragments. Using this approach, we can quickly generate DNA fragments that are subsequently decoded on an array, thus providing a huge increase in capability over conventional computers in solving Monte Carlo problems. Indeed, evolution itself can be thought of as one vast, on going Monte Carlo experiment. We will use pattern recognition algorithms to provide a digital readout. These innovations represent advances in current methods that allow us to rapidly decode the information present in biological samples.

Logical computations performed on our phylogenetic chip are the series of binary inputs representing branch points in the phylogenetic tree. In our system, random primer PCR provides a massively parallel approach to generating potential solution sets to a given problem. Our phylogenetic chip presents information as a pattern of known DNA fragments. Hybridization of the genomic solution set to our phylogenetic array identifies appropriate solutions (indicates a particular logic path) and eliminates (disregards) those possible solutions (DNA fragments amplified but not present on the chip) that are not relevant to the logic tree. Each spot on the array provides a binary response, but the inherent complexity of DNA fragments present on the array provides a huge increase in capability over conventional computers that can only register a zero or a one at each position.

Well known researchers in the field of biocomputing have developed DNA-based computational approaches that represent information as a pattern of molecules in a strand of DNA and have manipulated that information by subjecting it to various chemicals to alter the structure of the DNA strands. Each DNA strand represents one possible answer to the problem that the DNA computer is trying to solve. DNA strands are produced so that all conceivable answers are included. A drawback is that a new set of strands must be developed for each new problem to be solved. These DNA computers identify correct answers to the question being asked by simultaneously subjecting all DNA strands to chemical reactions that mimic mathematical computations performed by a conventional computer on each possible answer. In these DNA-based approaches, mathematical operations are performed with enzymes that alter the DNA based on the structure of the DNA present in a particular spot.

Our approach differs in several ways. We use random primer PCR to produce a solution set of DNA strands representing the genome of all biological species present in the sample. In our approach, hybridization between complementary DNA strands is the mathematical operation that is conducted in a massively parallel format. Each spot on our array (containing many copies of a DNA strand) represents a step in the logic path toward solving the problem. Our approach differs in that we do not have to make a new set of DNA for each new problem set. Furthermore, answering a question does not destroy our device. The DNA arrays can be stripped and hybridized to new samples. Our phylogenetic approach will allow us to answer many different questions using one chip. Once we have developed the sequences to answer a particular question, we can rapidly reconfigure and replicate patterns, much in the way that one can replicate and reuse code in conventional computers.

The first technology is a method by which we will generate a solution set of a complex mixture of random-primed labeled DNA fragments. These random DNA fragments will be synthesized from genomic bacterial DNA using short random primers and the polymerase chain reaction (PCR) incorporating a fluorescent tag. Classically, the PCR reaction uses longer (20-30 bases) paired primer sets for the specific amplification of a single nucleotide sequence. These primers bind to specific sequences within the genome that bracket the region of interest and serve as initiation points for DNA synthesis. The result of thermocycling in the PCR reaction is the synthesis of a large amount of a single polynucleotide sequence where the primer set defines the start and end sequences. In dramatic contrast to classical PCR, our approach utilizes much shorter primers (six to eight bases in length) that are synthesized as all possible combinations of the four base elements of DNA. This allows the primers to hybridize in random fashion to essentially all regions of the genome, and serve as initiators of DNA synthesis.

We have successfully demonstrated this technique of random primer PCR in our laboratory. This use of short primers present in excess and not as ordered pairs produces labeled DNA fragments of various sizes representative of the entire genome. Classical PCR results in a single band of DNA when analyzed by gel electrophoresis. Our random primed PCR product generates a smear of DNA in sizes ranging from 2,000 to 300 bases in lengths. By varying parameters such as cycle number, amount of template, amount of primer etc., we can control the size distribution of the amplified fragments.

The second innovation is the use of a high density DNA microarray to perform computational analysis of the random-primed DNA fragments comprising the solution set. Standard DNA microarrays are constructed as templates of thousands of genes for a specific organism or tissue. By comparing reverse transcriptase PCR from messenger RNA from both a control and experimental sample, one can analyze modulations of gene expression. Our system utilizes the high information density of the microarray for a very different application. Rather than looking for differential expression of known sequences, we are looking for the presence or absence of specific sequences in our solution set of DNA fragments generated by the random primer PCR. The array will contain up to tens of thousands of spots, each spot containing many copies of a particular known DNA sequence. The DNA in a particular spot will hybridize only with fragments in the amplified, labeled mix that share sequence identity. The interaction of DNA fragments in the labeled solution set with the immobilized, known DNA sequences on the microarray is random, but the binding of fragments in the solution set to fragments on the array is very specific. This interaction forms the basis of a highly parallel molecular computation. We have an Affymetrix ring and pin microarray machine in our laboratory for the construction of custom DNA arrays, as well as the necessary equipment for the generation of specific DNA sequences for the array.

The third innovative strategy is the approach to determine what DNA sequences are arrayed on the chip. These determinations are aided by the massive sequencing efforts in the scientific community that support the construction of phylogenetic diversity maps using published DNA sequences. Known regions of conserved and unique sequences of DNA will form the logic structure for our phylogenetic DNA chip. These DNA sequences will be immobilized on the array and function as a computational decision tree. Each spot, or series of spots, will represent a branch point in the phylogenetic tree that will be used to characterize and identify biological species present in a sample. Subsequent incubation of the chip with the solution set generated by the random primer PCR will result in hybridization of solution elements with the immobilized fragments. The hybridization between complementary strands is a mathematical operation that is conducted in a massively parallel fashion. The pattern of hybridization to the phylogenetic array will provide the outcome of the computation. Each spot on the array is asking a binary question, "Is this sequence present in the test sample?" The pattern of binary answers will be analyzed digitally.

One of the technological hurdles that must be overcome in DNA computing is reducing the number of computational errors from spurious interactions involving the DNA strands. We will array multiple sequences at each level of discrimination on the DNA chip. In terms of the DNA-based computations, we will optimize the size and structure of DNA fragments arrayed on our chip and the hybridization conditions used to identify complementary strands of DNA with true sequence identity. If needed, we will develop or modify optical reading software to read the pattern produced by the DNA computations with a high degree of accuracy. In addition, we will employ pattern recognition methods to rapidly and accurately compare the results of the DNA-based computation to known sequences to identify the species present.

The fourth element of our approach is the integration of a digital computer to employ pattern recognition algorithms to assist in read-out and analysis of the hybridization pattern identified by the incubation of the random primed sample DNA with the phylogenetic DNA chip. We will array DNA fragments to serve as information objects on the gene chip and use a commercial scanner resident in our laboratory to visualize the pattern. We will use pattern recognition methods to extract the probability that a target sequence is present or absent in the reaction mix. We can infer the presence or absence of a potential solution based on which probabilities are large versus which are small. We shall investigate two approaches:

Artificial Neural Networks. The probabilities are fed as inputs into a back propagation neural net that has been trained to recognize DNA hybridization patterns that solve the problem.

Bayesian Inference Nets. An expert develops probabilities that a solution is in the given reaction output given the presence or absence of a spot on the array (this is a problem based activity). The spot probabilities and these conditional probabilities are collated using well-established methods to construct the probability that a solution is present in the sample.

This approach allows us to integrate more sophisticated computational algorithms into out biocomputer. This addresses the issue of performing tasks biochemically that can more easily be done digitally. SAIC has a large repository of legacy software and expertise for implementing these technologies and has applied them in numerous contexts.

A unifying concept for biocomputing has been using biochemical reactions to implement Monte Carlo searches in combinatorial problems. The problem is encoded in such a way that it is possible to create a reaction mix that generates potential solutions to the problem at hand. The problem encoding is done in such that extract genuine solution is chemically possible. For example, Adleman encoded the Hamiltonian path problem by associating 20-mers to each node in a graph and encoding edges as 20-mer such that 10 bases on the 3' end could hybridize with the "from" node and the other 10 (on the 5' end) could hybridize to the "to" node. He then made a mix of these 20-mers (edges and nodes) and allowed a reaction to hybridize and ligate. By encoding the problem the way he did, he was able to infer that the longest polymer out of the reactor would be a solution. We propose to bring advanced technologies together to execute general problems of this form. Specifically, we will use random primer PCR to generate solutions to the computational problem, array specific sequences on the gene chip to encode the solutions, high density gene chip analysis to visualize the solutions, and advanced computation to infer solutions to the problem from the pattern on the gene chip.

Example 9

We are developing a novel, scalable DNA-based biocomputing technology that rapidly executes massively parallel searches to solve problems that are beyond the scope of conventional computational capabilities. Specifically, we will perform computations using biological information packets and a wet, content-addressable database with biological information objects arrayed in a biological matrix to determine the biological content of a sample. This approach will answer the question, "What is the phylogenetic representation within a particular sample of DNA?" This approach combines a randomly generated complex information set of labeled DNA fragments and performs a parallel computation with biological information objects immobilized on a DNA chip. The DNA chip represents a content-addressable wet database of high-density immobilized known DNA sequences. This computing approach involves the integration of four distinct technologies; DNA amplification, bioinformatics, DNA microarray, and pattern recognition technologies. In order to integrate these diverse disciplines, our team shall consist of a collection of biochemists, molecular biologists, computer scientists and mathematicians.

Current biological identification systems determine the presence of one, or a few, DNA sequences for characterization. Our system will perform a detailed analysis of the biological composition of a sample by fragmenting complete genomes into discrete, addressable biological information packets that can be analyzed by in parallel on a content-addressable wet DNA phylogenetic database chip. We believe this computational approach will provide the ability to characterize complex biological samples containing hundreds to thousands of biological elements simultaneously. The potential benefits to the DoD range from battlefield identification of biological warfare agents, including characterization of unknown pathogens, to the massively parallel identification of biological species in a clinical setting.

We will generate information packets consisting of a complex mixture of labeled DNA fragments representive of the genomes of biological elements in a sample. The information packets will be labeled by the incorporation of a fluorescently-labeled nucleotide. This initial step performs three key functions; first, it fragments the genome into discrete information packets; second, it amplifies the genome thereby providing redundancy of signal; and third, it incorporates a fluorescent label that allows the information packets to be analyzed in parallel by a wet, content-addressable database. The database will contain discrete information objects in the form of a high-density DNA microarray with known DNA sequences that represent branch points in the phylogenetic tree. Exposing the solution set consisting of biological information packets produced from DNA present in the sample to the array of known sequences at discrete locations on our microarray database will allow us to identify correct solutions. The interaction forms the basis of a highly parallel molecular computation to identify key in the template genomes.

We will use a commercial microarray reader read out the results computed by the wet database. We will employ pattern recognition algorithms to assist in read-out and analysis of the pattern on the DNA chip database. We will employ two approaches, neural networks and Bayesian inference networks, to register the pattern and infer the presence of various biological elements. Using prior knowledge of the immobilized sequences relative to their phylogenetic conservation, we will be able to identify the genomes represented in our original sample.

Technical Rationale

Introduction

We propose to develop a novel technique for performing computations in a biological matrix. Using a proprietary approach, we will fractionate massive amounts of data resident in biological genomes into discrete information packets. In addition, we will develop a compact, content-addressable wet phylogenetic database and use inherent properties of DNA molecules to perform complex computations in a massively parallel manner. Our approach has the ability to solve problems that are not addressable by conventional computers. Numerous researchers in the field of biological computation are using short DNA sequences to code information in DNA to use the nature of biomolecular interactions to solve computational problems. Rather than take this approach, we will exploit information encoded in larger DNA fragments to meet several of the goals and address several of the technical topic areas of this program. In addition, our approach will answer questions with relevance to DARPA and the Department of Defense (DoD).

We will use proprietary technology combining random primer DNA amplification and a phylogenetic DNA database chip to create a large solution set quickly, and conduct computations analyzed as a pattern of hybridized DNA fragments. The random-primed DNA aqueous amplification reaction will fragment, amplify, and label DNA present in a sample. These "biological information packets" compose partial answers to the question, "What is the biological composition of the sample?"

The aqueous solution set will be exposed to a content-addressable wet database, or DNA microarray used to store and retrieve specific DNA sequences or "biological information objects" on a solid substrate. We will identify, generate and array DNA sequences that represent branch points in a phylogenetic tree. For example, we will array some DNA sequences that are conserved in all living things, some that are conserved in bacteria, some that are conserved in Gram positive bacteria, etc. until we travel from the trunk of the tree out smaller and higher branches to the twigs and leaves that represent DNA sequences that are specific to a strain or biovar of a particular bacteria.

This approach of arraying known sequences of varying phylogenetic diversity using a microarray format represents a scalable, high-density, content-addressable wet database. The interaction of the partial answers in the aqueous solution with known branch points from the phylogenetic tree arrayed on a DNA chip represents a massively parallel computation that rapidly characterizes the biological nature of the sample. We will use pattern recognition algorithms to provide a digital readout of the biological computation. These innovations represent advances in current methods that allow us to rapidly decode the information present in biological samples.

Spots on our phylogenetic chip are the series of binary inputs representing branch points in the phylogenetic tree. In our system, random primer DNA amplification provides a highly parallel approach to generating potential solution sets to a given problem. Our phylogenetic chip presents information as a pattern of known DNA fragments. Hybridization of the genomic solution set to our phylogenetic array identifies appropriate solutions (indicates a particular logic path) and eliminates (disregards) those possible solutions (DNA fragments amplified but not present on the chip) that are not relevant to the logic tree. Each spot on the array provides a measurable response, but the inherent complexity of DNA fragments present on the array provides a huge increase in capability over conventional computers that can only register a zero or a one at each position.

This effort provides a unique contribution in two technical topic areas of relevance to DARPA. First, we will develop a wet, content-addressable database using biosubstrates on a solid support matrix. This database, or DNA microarray, will embody a proprietary phylogenetic approach to characterize the biological content of complex samples. Second, we will demonstrate the computational capabilities of DNA information packets generated from a sample and interrogated by interactions with the content-addressable wet phylogenetic database DNA chip. Analysis of the pattern produced on the chip will provide phylogenetic information relative to the original DNA in the sample.

In addition, our initial problem set will address a pressing DoD need to identify and characterize biological threat organisms and pathogens that threaten to compromise our fighting capability. Specifically, this technology can be used to characterize or "compute" the biological composition of any environment air, water, or clinical samples, for example. Our initial effort will provide distinguishing information relative to prokaryotic organisms. This same technical approach is applicable to analysis of higher level organisms. As the genomes of humans and other mammals are elucidated, one can envision the generation of database chips that can genotype individuals with high fidelity. These chips could be used for forensic analysis or medical profiling, for example. On the battlefield, this technology could be used to identify the presence of toxic biological substances in the environment.

Two major concerns of the DoD biodefense community are the characterization of unknown organisms and the identification of genetic manipulations for the construction of chimeric biological organisms. This approach addresses both of these issues. In the case of an unknown organism, we will not have DNA sequences that are unique, however there will be conserved sequences identified. The presence of these conserved sequences will provide partial characterization. In order to address genetic manipulations we can array both structural as well as virulence genes on the database. If we observe virulence genes without the structural genes from the same organism, this provides indication that these virulence genes are contained within another organism whose phylogenetic pathway is identified by the database.

Current DNA-based approaches to analysis of biological materials identify the presence of one, or a few, unique target sequences for a specific organism. These protocols use very specific primers, or start points, to amplify and label specific DNA sequences using the polymerase chain reaction (PCR) technology. Generally, a separate assay is used to detect a particular organism. Using standard methodologies, if one wants to ask hundreds of specific questions of a given sample, one must conduct hundreds of individual PCR reactions, each with slightly different experimental conditions. The throughput of this type of approach is extremely limited. Worse yet, if the biological threat agent or pathogen is not among those for which this type of DNA based test has been developed, classical microbiology methods must be used. These procedures require that the organism first be cultured and then characterized in the laboratory. This process takes days to weeks to complete. In contrast, our proprietary biocomputational approach uses short, random primer sequences to amplify essentially all DNA present in a sample combined with a phylogenetic DNA chip to characterize biological content of such samples. This method fragments, copies and labels DNA present in a sample and uses the microarray format to perform a massively parallel query of a phylogenetic database on arrayed on a DNA chip.

Starting with a complex sample containing genomic DNA from one or more organisms, our first task is to convert this complex information set into information objects that can be analyzed by our chip database. In order to accomplish this, we must perform four key manipulations of the data. First, we must construct information objects in size fragments that can be analyzed by our wet database. Second, we must incorporate a visualization tool into these information objects so we can track their location on the database. Third, we must amplify the genomic DNA so that we have redundancy of sequences. Fourth, we must ensure the entire genome has been fragmented, labeled and amplified.

We can achieve these four tasks using "random primers" for the initiation of DNA synthesis. The objective of using random primers is to provide initiation sites for DNA amplification in many regions of the genome. For example, random primers of six nucleotides in length, composed of four different DNA bases, results in 4096 different potential sequences. These short sequences will find many matching sequences in the genome to pair to and initiate synthesis of new DNA strands. We have conducted preliminary experiments using octamers that have 65,536 different sequence possibilities. These random primers are easily available and inexpensive. We incubate the primer mix with prepared genomic DNA, a mixture of labeled and non-labeled nucleotide triphosphates (building blocks of DNA) and a DNA polymerase. This reaction generates DNA information objects that contain specific subsets of genetic information from the template genome.

Random primer DNA amplification generates a diverse representation of the template genome. Not all of the synthesized DNA will contain the key sequences that will be immobilized on the database chip. Some regions are illustrative of conserved sequences between the two genomes, while other regions are unique. The hybridization patterns generated would each hybridize with the conserved regions, but demonstrate by hybridization with unique sequences.

The biocomputational approach described in this proposal is scalable on many levels. The first step of genome fragmentation and labeling is performed in an aqueous solution. Standard reactions are performed in microliter volumes. It is possible to scale up this reaction four to five orders of magnitude higher, but cost of reagents would increase correspondingly. Robotics are available to automate many routine laboratory procedures such as DNA amplification reactions and hybridization and wash procedures. Automation has dramatically increased the throughput of genome sequencing efforts over the past decade. Our content-addressable wet database is a DNA microarray that is scalable in at least two ways. First, the density of spots can be increased. The first arrays produced in the mid 1990's contained hundreds of spots. Recently, researchers have achieved hundreds of thousands of spots on a single microscope slide representing three orders of magnitude improvement. Another way to scale this technology is to use multiple arrays to obtain one or more orders of magnitude scalability. Several commercial entities offer robotics for automation of array construction, storage, and archiving. Finally, there are large scale sequencing efforts underway to elucidate the genomes of many bacterial and animal species. We intend to leverage these efforts to improve the fidelity and expand the applicability of our approach.

Our approach is to identify conserved and unique sequences that will provide error resilient characterization of the biological elements in the sample. Error resilience will be achieved by arraying DNA sequences that allow us to discriminate all relevant branch points in the phylogenetic tree, from sequences common in all life to those that are found only in a particular strain or biovar of a bacterial species. One or more breaks in this phylogenetic path would result in a determination associated with a lower confidence level. On the other hand, a result that is difficult to characterize might be suggestive of a previously uncharacterized organism or one that has been subject to genetic manipulation. In this instance, our phylogenetic characterization can be used provide a rapid initial prediction that can be used to focus more detailed characterization by other methods.

We will provide a detailed technical approach and constructive plan for each of the technical tasks in the section below. These hybridization regions will be interrogated using a commercial microarray reader in our laboratory. The output will be analyzed with software and analytical tools developed in the Pattern Recognition task described below using conventional computer technology.

The process outlined above represents a near-term application and benefit of biomolecular computational systems. In fact, the overall system is a hybrid of biomolecular and conventional computing technologies, with each performing a portion of the task that the other currently cannot. Outlined below, in greater detail, are the technical tasks and milestones required for the successful completion of this project.

Generate Solution Set

In order to extract meaningful information from genomic DNA for biological computing, we must first reduce the information into smaller packets of information. These information packets must also contain a label that makes them addressable by a readout device. Our strategy to fractionate and label the genome templates involves random primer initiated DNA synthesis with the incorporation of a fluorescent molecule (approximately 1 in 25 bases). We propose to use a DNA polymerase with short random primers to serve as initiation sites for DNA synthesis. This allows DNA fragments to be produced that are copies of many different regions of the genome. Label will be incorporated using a fluorescently-labeled deoxynucleotide triphosphate (dNTP) or base. We can adjust the intensity of signal to some degree by adjusting the ratio of labeled to non-labeled base. Incorporation of too many fluorescent molecules will interfere with the DNA hybridization.

We will optimize the random DNA amplification to generate a solution set using primers of six to nine bases in length. Synthesis of these random primers is a routine and inexpensive procedure. Similarly, DNA polymerases used with these random primers are standard molecular biology reagents. Genomic DNA will be heated to separate the double stranded DNA then cooled rapidly to expose single stranded sequences that are the templates for synthesis of new DNA strands. The random primers will bind in these open regions and serve as initiators of DNA synthesis using a DNA polymerase.

A key step in this task is to experimentally determine the conditions by which, utilizing random short primers, we can fragment, label, and amplify genomic DNA in a representative fashion. We have conducted preliminary experiments in our laboratory and are able to amplify, label and fractionate template genomes in this fashion. Classical PCR results in a single band of DNA when analyzed by gel electrophoresis. Our random-primed DNA amplification product generates a smear of DNA in sizes ranging from 2,000 to 300 bases in lengths. By varying parameters such as amount of template, amount of primer etc., we have modulated the size distribution of the amplified fragment. In these initial experiments, we have incorporated biotin as our label. Biotin is a small molecule that allows us to visualize DNA by eye on an opaque substrate, such as nylon. We have used this in combination with avadin linked peroxidase enzymes to generate a black precipitate.

In our current protocol, fragments of genomic DNA are randomly amplified and simultaneously labeled for future use in the non-radioactive detection of specific DNA targets. This is done by adding random primers (hexamers and octamers have been used) which are annealed to a denatured (single-stranded) DNA template, and extending the fragment using a Klenow enzyme in the presence of a biotin-labeled dNTP. This process results in considerable net DNA production, with amplification resulting in a 10-40 fold increase in the amount of starting DNA. The amount of amplification is dependent on the amount of starting material, the concentration of primers and dNTPs, and the incubation time.

We propose to conduct initial experiments using this preliminary system already established in the laboratory while generating microarrays on microscope slides in parallel. Hybridizations are performed on nylon membranes to which DNA is bound using a dot blot apparatus. Using this system we have provided preliminary evidence that this approach can distinguish host from non-host immobilized DNA. We have previously demonstrated that the amplification approach utilizing the Klenow enzyme is a successful method for making a probe that can distinguish DNA between two bacterial species. Using this method, an experiment was designed where various DNAs from *Escherichia coli* and *Bacillus subtilis* were prepared and hybridized with random-primed probe from *E. coli*. The blot contained PCR products that are exclusive to *E. coli* and *B. subtilis*, as well as PCR products that are common between the two species but still hold a small degree of variation. The probe was prepared by annealing random primers (octamers) to digested *E. coli* (genomic) DNA fragments and extending these primers via the Klenow enzyme. This extension was done in the presence of non-labeled dNTPs and a biotin-labeled dNTP. The probe was purified to remove unincorporated dNTPs, and then quantified by an $A_{260}$ measurement.

After incubating a specific amount of probe with the blot in an overnight hybridization, the blot was washed in a series of buffers and developed for detection of the bound probe. Among the PCR products mentioned above, the DNAs that are specific to *E. coli* showed a signal; however, the *B. subtilis*-specific DNAs showed no signal. Furthermore, the probe showed a specificity for the common DNAs by presenting a stronger hybridization signal for the DNA produced from *E. coli*, compared to the weaker signal for the DNA produced from *B. subtilis*. These results indicate that we are able to use random-primed DNA amplification to generate information objects that hybridize specifically to host genome, but not to foreign DNA. This pilot experiment demonstrates the fundamental soundness of the approach for differentiating species DNA.

To establish that our product is representative of the entire genome, we can perform a restriction digest of genomic DNA and hybridize it with the fragmented, labeled, amplified DNA. Restriction enzymes cleave DNA at specific sequences. The DNA sequence, or restriction site, that the enzyme recognizes determines the number and size of DNA fragments produced from the starting DNA. We will digest genomic DNA using a restriction enzyme that generates less than one hundred fragments. The resulting DNA will be loaded on both low and high-density agarose submarine gels to provide separation at both the low and high molecular weight ranges. After documenting the staining intensity with Cyber Green dye, the DNA will be electrophoresed to a nylon membrane. Following cross-linking and blocking, the membrane will be hybridized with our random-primed labeled DNA information objects. Visualization will be accomplished by binding of avadin linked alkaline phosphatase with subsequent substrate addition. If our genome amplification is truly random, the staining pattern from restricted DNA, should correlate with the intensity of labeled, randomly amplified DNA that hybridizes to each of the restricted fragments. If the enzymatic visualization pattern demonstrates greater or lesser intensity of any of the bands, this will indicate nonrandom amplification. If this is true, we will have to make adjustments in the analysis protocol of some of these regions are chosen for are array database.

Once we have determined the conditions to uniformly label the entire genome, we must determine the optimal fragment length and labeling conditions for hybridization of amplified DNA to the microarray. The percentage of label will be a tradeoff between efficiency of hybridization and intensity of the signal from hybridized DNA. Fragments that are too large are expected to have decreased hybridization efficiency. Fragments that are too small may not have the necessary degree of uniqueness to hybridize specifically, thereby increasing background noise. This task will be performed in concert with the task to establish optimal hybridization conditions.

Content-Addressable DNA Microarray Phylogenetic Database

The second technical task is the fabrication of a high-density DNA microarray database for computational analysis of the random-primed DNA information objects comprising the solution set. Using this technology, investigators have patterned tens of thousands of DNA sequences representing thousands of genes on single chips. The preponderance of literature and patents on microarray technology are on the use of these DNA chips to identify gene expression and regulation as a function of external stress or disease condition. In this approach, investigators synthesize complementary DNA (cDNA) from the message (mRNA) in the cell that indicates a gene is expressed and incorporate a fluorescent label. A control sample is labeled with one fluorescent molecule, Cy-3 for example, and an experimental sample is labeled with a different fluorescent molecules such as Cy-5. The samples are mixed and hybridized with a microarray of genes from the organisms of interest and the differential hybridization of control versus experimental sample.

Our system utilizes the high information density of the microarray for a very different application. Rather than looking for differential expression of known sequences, we are looking for the presence or absence of specific sequences in our solution set of DNA information objects generated by the random primer DNA amplification. The array will contain up to tens of thousands of spots, each spot containing many copies of a particular known DNA sequence. The DNA in a particular spot will hybridize only with fragments in the amplified, labeled mix that share sequence identity. The interaction of DNA fragments in the labeled solution set with the immobilized, known DNA sequences on the microarray is random, but the binding of fragments in the solution set to fragments on the array is very specific. This interaction forms the basis of a highly parallel molecular computation.

We will construct a DNA microarray by spotting small volumes of a solution containing DNA onto the slide or membrane. The DNA is then immobilized and denatured to allow subsequent hybridization with amplified labeled DNA fragments in aqueous solution. Our approach requires only a single fluorescent molecule since we are looking for a binary response, the presence or absence of a particular location on the array. We will use established computer technology to image and analyze the pattern resulting from the biological computation. Some modification to existing visualization and software may be necessary to optimize the readout using our approach.

Our efforts to produce an array of DNA fragments that represent the branch points of a phylogenetic tree will be aided by massive sequencing efforts in the scientific community that support the construction of phylogenetic diversity maps using published DNA sequences. Known regions of conserved and unique sequences of DNA will form the logic structure for our phylogenetic DNA chip. These DNA sequences will be immobilized on the array and function as a computational decision tree. Each spot, or series of spots, will represent a branch point in the phylogenetic tree that will be used to characterize and identify biological species present in a sample. Subsequent incubation of the chip with the solution set generated by the random primer PCR will result in hybridization of solution elements with the immobilized fragments. The hybridization between complementary strands is a mathematical operation that is conducted in a massively parallel fashion. The pattern of hybridization to the phylogenetic array will provide the outcome of the computation. Each spot on the array is asking a binary question, "Is this sequence present in the test sample?" The pattern of measurable answers on the array will be analyzed digitally.

The DNA sequences identified above represent key information elements for the analysis of uncharacterized DNA information solution sets. By generating and immobilizing these key sequences through standard DNA amplification technologies, we will construct a high-density array that will constitute a content-addressable wet database used to analyze and compute the presence of key information packets generated. We will construct the array using the Affymetrix 470 Arrayer resident in our laboratory.

Massively Parallel Analysis of Solution Set

The third technical task is the interrogation of the labeled biological information packets in a sample with a high-density phylogenetic DNA database. The database, arrayed on glass slides will be hybridized with the DNA information packets generated by the random-primed DNA synthesis. Initial hybridizations will be conducted using standard microarray hybridization protocols. Modifications will be made in both the hybridization and wash conditions to optimize the signal strength and to minimize nonspecific binding. Computations performed on the microarray will be subject to many of the technical issues that face other investigators performing microarray analysis. One notable exception is that we are not performing a mixed incubation with two separately labeled DNA samples. We will be interested in the spot intensity, not ratio of two emission wavelengths from two different fluors. However, we will have to contend with issues of spot uniformity, background staining, and sensitivity. We will use the technical literature and network with our established network of investigators in the microarray field to address these issues.

We have conducted initial experiments using nylon membranes in a macro array format. Our protocol includes denaturing a randomly amplified DNA and mixing it with a commercially available hybridization buffer, followed by incubation with a blot or slide that contains the target DNA of interest. In these experiments, we used biotin to label the DNA fragments followed by incubation with avidin and a peroxidase enzyme to form a colored precipitate. In future experiments, we will incorporate a fluorescent label, thus eliminating the need for the series of chemical reactions needed to visualize by eye.

We will use published incubation and wash conditions in microarray hybridization experiments conducted under this effort. Incubation times and temperatures vary and must be optimized for a particular application. To optimize hybridization conditions for this application we will experiment with different times and temperatures to determine optimal conditions to increase the rate and fidelity of hybridization of the labeled biological information packets to the content-addressable wet database. We will use the Applied Precision ArrayWoRx resident in our laboratory to visualize and capture the pattern of exact matches.

Following hybridization, blots or slides are washed in a series of salt-containing buffers at times and temperatures that are must also be optimized for a particular application. Under desirable conditions, these washes remove DNA sequences that did not bind tightly to the desired target sequence(s) on the array. The sequences that remain bound have perfect sequence identity with the DNA spotted at a particular location on the array. We will determine conditions to reveal the degree of DNA sequence similarity between the biological information packets generated from a sample and the target DNA sequences on the microarray, based on the color intensity of the bound DNA sequences.

Bioinformatics

The rapidly expanding field of bioinformatics and functional genomics provides a foundation for the fourth task. The phylogenetic representation contained on our content-addressable wet database requires that we can identify specific DNA sequences (each of approximately 500 nucleotides) beginning with highly conserved sequences, to progressively more unique sequences associated with certain types of organisms. The ability to map these sequences to individual organisms and groupings of organisms is key to our computational algorithm. This would have not been possible only a few years ago. The massive sequencing efforts (The Institute for Genomic Research has 134 organisms either sequences, or in progress) have overcome one technical hurdle for this type of analysis.

We will use existing phylogenetic databases as well as available genetic sequence search engines to identify candidate sequences for our database chip. Up to now, the major focus of molecular phylogenetic analysis has been on the 16S ribosomal subunit. We will augment this well developed approach with our own analysis of the growing literature of type-two gene molecular phylogeny selecting a sufficient number of genes to result in the high reliability of identification we require. We expect that we will identify about twenty-five different genes that are characterized by a near universal representation among the three kingdoms of living cells. This choice will be motivated by the likelihood of a common ancestor within each gene before the branching into three kingdoms and a diversity of sequence that will provide a high aggregate reliability for distinguishing an organism down to the genus or species level. Although significant literature exists relative to the phylogenetic conservation of the bacterial 16S ribosomal DNA sequences, we do not feel there is sufficient diversity of sequences greater than 200 bases to provide the necessary discrimination for our computational purposes. These regions do, however, provide key sequences for identifying DNA as bacterial.

Significant progress has been made in terms of identifying DNA sequences that are unique to specific bacterial species. These sequences form the basis of most polymerase chain reaction (PCR) based bioassay systems. The U.S. Government has made significant investments in the identification of unique primer pairs for the characterization of pathogens for our biodefense community. Our plan is to leverage this information funded by the Government. We will use these identified primer pairs and sequences to provide the most specific levels of discrimination on our database chip, leveraging previous investments.

A key element of this approach is the identification of information packets that represent key features of the larger information set that composes the genome. These key features will be used to distinguish different organisms at the genus and species level. We will leverage past and present sequencing efforts to identify conserved and unique regions of bacterial genomes. Our goal is to generate multiple mutually supporting parallel representations of DNA-based phylogenetic tree on our wet content-addressable database. We will initially use share-ware and commercially available software for gene sequence comparison and analysis. In conjunction with this initial analysis, we will identify structural and functional elements in the genome that are "key features". We will develop software to automate the identification of these features. In addition, we will perform mathematical calculations to determine the number of sequences needed to conclusively distinguish one genus from another and one species from another.

Pattern Recognition, Processing and Decision Making

The fifth technical task is the integration of a digital computer to employ pattern recognition algorithms to assist in read-out and analysis of the hybridization pattern identified by the incubation of the random-primed sample DNA with the phylogenetic DNA chip. We will array DNA fragments to serve as information objects on the gene chip and use the Applied Precision ArrayWoRx scanner resident in our laboratory to visualize the pattern. We will use pattern recognition methods to extract the probability that a target sequence is present or absent in the reaction mix. This approach allows us to integrate more sophisticated computational algorithms into out biocomputer. This addresses the issue of performing tasks biochemically that can more easily be done digitally. We have a large repository of legacy software and expertise for implementing pattern recognition technologies in equivalent contexts.

Once we have hybridized the DNA to the gene chip, we must then read and process the measurable pattern that has been encoded by the DNA. There are two processing activities that we will address:

We will develop methods associated with scanning a gene chip such as registering the scanned data to the experimental design of the chip and interpreting the intensities of the detected patterns as probabilities that hybridization has occurred.

We will develop inference rules about the organisms that are present based on the tag hybridization probabilities.

Extracting Hybridization Probabilities

We propose to execute the develop methods to register scanned data using fairly standard registration and normalization technologies. Once the chip has been incubated and scanned, the first step in processing will be to extract oligomer hybridization probabilities. The hybridization probability (HP) is defined as the probability that a given oligomer tag represents DNA present in the environmental (or clinical) sample. In an ideal world, we would be able to state with certainty that a DNA sequence tag is present in the sample or it isn't (i.e. HP would be 1 or 0). Based on the signal to noise ratio of each spot in the array, we will determine if an authentic signal is present and with what "P" value. Because of the high level of redundancy in our chip design, we expect an extremely rich and correlated pattern of hybridization signals with very high information content. This pattern will be translated into a "most probable" identification of the unknown organism with an associated level of confidence.

Our approach to generating HPs is as follows. An Applied Precision ArrayWoRx scanner in our will produce an intensity image. In our experimental approach we are not developing ratios (the traditional approach in microarray technology)—we are measuring absolute concentrations based on fluorescence. This means that the data can be represented as grayscale images as opposed to the red-to-yellow-to-green of a typical gene chip experiment. The scanner produces an image that must then be registered to the experimental design of the chip. This is needed because we need to match oligomer tags with intensity responses in the scanned image. A typical application would be to register a model of an airfield to an image of an airfield so that we need only make inferences in the "interesting" areas. We do not anticipate the registration problem to be any more difficult in an environment where we have a more control in the "geography" (i.e. the layout of tags on the gene chip). We propose to use the technologies that we have applied in model registration for satellite imagery in this context.

After registration, we will extract the HPs based on the intensity information in each cell. The goal will be to turn the intensities into probabilities. We will do this with reference spots, which include a range of tags that cover all known sequence variants of a highly conserved family of genes. This will provide expected positive values as well as many gradations of signal down to negative signals. We intend to use the 16S ribosomal RNA as this reference because it is universal in all cells and is conserved at the nucleotide level. In addition, an enormous database of different sequences already exists in the literature. This will represent several DNA tags that are known to hybridize well to all organisms of interest and another set that are known not to hybridize at all to organisms of interest. These tags will provide the range of meaningful intensities that can be expected. To extract probabilities we will use detected intensities along with knowledge of a function that maps intensity to degree hybridization. As an initial starting point, we propose to measure hybridization as a linear function of the area and intensity of a spot.

Drawing Inferences Based on HPs

Once we have the HPs, we can infer the presence or absence of organisms based which HPs are large versus which are small based on the pattern of HPs. We propose to investigate two approaches:

Artificial Neural Networks. The HPs are fed as inputs into a back-propagation neural net that has been trained to recognize DNA oligomer patterns of the organisms of interest. There is an output node for each organism of interest.

Bayesian Inference Nets. An expert develops probabilities that an organism is present given the presence or absence of a tag. The HPs and these probabilities are collated using a well established algorithm ([Pearl], [Neapolitan]) to construct the probability that an organism is present in the sample.

The network can be trained in two ways. Both involve the use of the back-propagation algorithm [Rumelhart, et al.]. One way to train the network is simply to use a binary vector indicating the tags that are known to be in an organism along with the associated organism as input/output pairs. An alternate approach would be to run gene chip experiments on samples known to contain a single organism and use the HPs generated from these experiment as inputs with the output determined by the organism. For this effort, we shall focus our investigation on the first approach.

We have a large library of neural network legacy software that has been developed in house and expertise in neural networks and experience in applying neural networks for pattern recognition.

The Bayesian inference net is an alternate approach to classification based on a probabilistic measure of a set of features (i.e. the HPs). We propose to investigate this approach in the final phase of the contract.

To see how Bayesian inference nets work, suppose we had only one oligomer tagged, say tag A, and we knew that the probability that *E. coli* is present in the sample given tag A is present on the gene chip is 0.9 and the probability *E. coli* is present given tag A is NOT present is 0.3 (these two probabilities do not need to sum to 1 since they are conditioned on different events). The probability that *E. coli* is present in the sample based solely on the evidence of the THP for tag A in FIG. 5 (THP=0.3) is:

$$Pr(E.coli \text{ is present}) = Pr(E. \text{ coli given Tag } A \text{ is present})$$
$$Pr(\text{tag } A \text{ is present}) + Pr(E. \text{ coli given Tag } A$$
$$\text{is not present})Pr(\text{tag } A \text{ is not present})$$
$$= .9 \cdot .3 + .3(1 - .3)$$
$$= .48.$$

This is a simple calculation when working with a single organism and a single tag. When working with more than one organism and more than one tag, one can still do the calculation but it requires a more sophisticated algorithm for collating the probabilities and a fair amount of input from an expert who can assert something about the probability of an organism being present given a tag is present or is not present. The algorithmic approach to collating these probabilities is the use of Bayesian inference nets.

We have implemented the algorithms used in Bayesian inference nets. Although we have no legacy code at this time, we have a support library of the major data structure required to implement the algorithms. Our team has the expertise required to generate the conditional probabilities need to make this technique work.

Advantages and Disadvantages of Neural Nets vs. Bayesian Inference Nets

Neural nets have the distinct advantage of being easier to train. The expert need only provide a list of oligomer tags expected to be present in the organism as opposed to generating a pair of probabilities for each tag/organism combination. Alternatively, the tags can be selected at random and a neural net is trained based on experimental behavior of the gene chip. The disadvantage of this approach is that we are surrendering the training of the decision process almost entirely to the computer. This can be disconcerting especially in instances where our procedure will be used to make clinical evaluations.

The Bayesian inference net approach is certainly more rigorous than the neural net approach but rigor comes with a cost. An expert has to construct probabilities that an organism is present given a oligomer tag is (or is not) present for each organism/oligomer pair. This task can be automated to some extent by using genome libraries and prior probabilities for the presence of each organism. The great advantage of using inference nets is that the networks are more semantically meaningful and it also possible to include intermediate hypotheses such as a tag indicating the presence of a grosser feature (e.g. Gram positive vs. negative) which in turn implies the presence of an organism. In addition, one can trace conclusions drawn by the system to specific assumptions. This is desirable for a system that will evaluate biological samples from battlefield and clinical situations.

In order to provide program integration and assess our technical progress, we will implement a series of Technology Assessment experiments. These experiments will be conducted at six month intervals and be designed to exercise the latest developments in each of the tasks of the project. The goal of these experiments is to demonstrate the biocomputational capabilities of the developing system. They will consist of a generation of a random primed set of information objects being hybridized to the latest phylogenetic microarray for computational analysis. The hybridization and washing protocol will be the most advanced to date. Subsequently, our reader will read the microarray database, and the data transferred to our analysis software for processing and interpretation. The first experiment will be limited to two organisms, but following experiments will increase the number of organisms and the number of information objects represented on the database chip.

As the scientific community has demonstrated with regularity, significant advances frequently occur at the interfaces of disparate technical disciplines. In keeping with this successful model, our proposed project also involves the integration and leverage of numerous diverse technologies. Merely bringing technologies together does not make for a successful program. It is essential that there be team members that have track records of providing bridges between the disciplines. In this project, we are merging the biological community with the mathematical and computational communities.

Comparison with Other Approaches

Well known researchers in the field of biocomputing have developed DNA-based computational approaches that represent information as a pattern of molecules in a strand of DNA and have manipulated that information by subjecting it to various chemicals to alter the structure of the DNA strands. Each DNA strand represents one possible answer to the problem that the DNA computer is trying to solve. DNA strands are produced so that all conceivable answers are included.

A unifying concept for biocomputing has been using biochemical reactions to implement Monte Carlo searches in combinatorial problems. The problem is encoded in such a way that it is possible to create a reaction mix that generates potential solutions to the problem at hand. The problem encoding is done such that extracting a genuine solution is chemically possible. For example, others have encoded the Hamiltonian path problem by associating 20-mers to each node in a graph and encoding edges as 20-mer such that 10 bases on the 3' end could hybridize with the "from" node and the other 10 (on the 5' end) could hybridize to the "to" node. By making a mix of these 20-mers (edges and nodes) and allowing a reaction to hybridize and ligate, it may be possible to infer that the longest polymer out of the reactor would be a solution.

The approach other groups to biocomputing involves binding a solution set to the surface of a DNA chip and then progressively constructing an answer by (enzymatically)

digesting away false answers. This has the potential disadvantage of being very slow (limited by the digestion process). Our approach involves drawing the final inference using a digital computer to process the spot pattern on a DNA chip. This integrates the use of digital technologies for solving a portion of the problem for which computers are classically very efficient. This avoids attempting to do something biologically that can be done more efficiently with digital computers.

A drawback of these approaches is that a new set of strands must be developed for each new problem to be solved. These DNA computers identify correct answers to the question being asked by simultaneously subjecting all DNA strands to chemical reactions that mimic mathematical computations performed by a conventional computer on each possible answer. In these DNA-based approaches, mathematical operations are performed with enzymes that alter the DNA based on the structure of the DNA present in a particular spot.

Our approach differs in several ways. We use random primer DNA amplification to produce a solution set of DNA strands representing the genome of all biological species present in the sample. In our approach, hybridization between complementary DNA strands is the mathematical operation that is conducted in a massively parallel format. Each spot on our array (containing many copies of a DNA strand) represents a step in the logic path toward solving the problem. Our approach differs in that we do not have to make a new set of DNA for each new problem set. Furthermore, answering a question does not destroy our device. The DNA arrays can be stripped and hybridized to new samples. Our phylogenetic approach will allow us to answer many different questions using one chip. Once we have developed the sequences to answer a particular question, we can rapidly reconfigure and replicate patterns, much in the way that one can replicate and reuse code in conventional computers.

Several groups are focusing their efforts on developing DNA-based devices, which can solve complex logic calculations of the NP complete category (Adleman, 1994). These include the Hamiltonian sort problems (Adleman, 1998) and the SAT problem (Liu et al., 2000). This is a very important class of problem and worthy of significant effort. However another class of problem of the table look-up type is naturally suited to DNA-based molecular computing. These problems have immediate and important applications that are very relevant to present health issues such as identification of contagious agents and treatment of infectious illness.

This specific and highly valuable type of computation that is well suited to molecular computing involves determining the phylogenetic relationships between different organisms (Kitazoe et al., 2001 and Liberles et al., 2001). The problems normally require the laborious sequencing of an organism followed by exhaustive sequence comparisons using conventional computational methods such as the Basic Local Alignment Search Tool (BLAST) algorithm. We propose that sufficient discovery of critical genotypic features already provides an alternative approach where random representations of an unknown organism made by PCR can be compared against our proposed wet database containing tens of thousands of sequences each representing distinctive sequences. The value of such a search is realized by this massively parallel comparison of information in many different gene families. Each of which represents an independent molecular evolutionary tree. The sum of these comparisons will be the determination of the identity of the unknown organism with high reliability to practically any level of confidence desired.

While the majority of the research on molecular evolution has previously focused on the ribosomal gene complex (Woese, 2000), recent comparison of measured and calculated secondary protein structure has allowed similar studies of type-two genes (Geourjon et al., 2001). Recent efforts have branched out to provide extremely valuable information regarding particular gene families and their evolutionary characteristics such as: TRAF a RING-finger protein (Grech et al., 2000), TRAM, a predicted RNA-binding domain (Anantharaman et al., 2001), various small-molecule-binding domains (Anantharaman et al., 2001B) and START domain superfamily (Ayer et a!., 2001). Using the clusters of orthologous groups (COG) database (Tatusov et al., 2001), significant progress has been made in defining the similarities and differences in the genomes of members of prokaryotes, archaea and eucaryotes providing a powerful means to determine lineage specific gene sequences Natale et al. (2000). In fact, deeper comparisons of protein tertiary structure for products, which were not considered related because of extreme sequence divergence, can now be shown to derive from a common ancestor, Aravend & Koonin (2000). This indicates the extreme discrimination possible from comparison of members of some gene families. We intend to leverage information from these studies in development of our phylogenetic DNA database concept.

While there are numerous software packages for processing DNA chips (e.g. Axon, Rosetta, etc . . . ), such processing is still at primitive stage insofar as the application of advanced pattern recognition algorithms. At their most advanced, existing commercial packages have focused on wrapping a graphical user interface around component technologies such as singular value decomposition (SVD) or K-means clustering and adding some visualization capability. Our computational work shall apply advanced algorithms to microarray data to answer a clearly defined scientific question what organisms exist in an environmental sample.

BIBLIOGRAPHY

Adleman L M. Molecular computation of solutions to combinatorial problems. Science 1994 Nov. 1 1; 266(5187): 1021-4.

Adleman L M. Computing with DNA. Sci Am 1998 June; 279: 54-61.

Altschul S F, Gish W, Miller W, Myers E W and Lipman D J. Basic local alignment search tool. J Mol Biol 1990 Oct. 5; 215(3):403-10.

Anantharaman V, Koonin E V and Aravind L. TRAM, a predicted RNA-binding domain, common to tRNA uracil methylation and adenine thiolation enzymes. FEMS Microbiol Lett 2001 Apr. 13; 197(2):215-21.

Anantharaman V, Koonin E V and Aravind L. Regulatory potential, phyletic distribution and evolution of ancient, intracellular small-molecule-binding domains. J Mol Biol 2001 Apr. 13; 307(5):1271-92.

Aravind L and Koonin E V. The alpha/beta fold uracil DNA glycosylases: a common origin with diverse fates. Genome Biol 2000; 1(4):RESEARCH0007.

Geourjon C, Combet C, Blanchet C and Deleage G. Identification of related proteins with weak sequence identity using secondary structure information. Protein Sci 2001 April; 10(4):788-97.

Grech A, Quinn R, Srinivasan D, Badoux X and Brink R. Complete structural characterization of the mammalian and *Drosophila* TRAP genes: implications for TRAF evolution and the role of RING finger splice variants. Mol Immunol 2000 August-September; 37(12-13):721-34.

Iyer L M, Koonin E V and Aravind L. Adaptations of the helix-grip fold for ligand binding and catalysis in the START domain superfamily. Proteins 2001 May 1; 43(2): 134-44.

Kitazoe Y, Kurihara Y, Narita Y, Okuhara Y, Tominaga A and Suzuki, T. A new theory of phylogeny inference through construction of multidimensional vector space. Mol Biol Evol 2001 May; 18(5):812-828.

Liberles D A, Schreiber D R, Govindarajan 5, Chamberlin S G and Benner S A. The adaptive evolution database (taed). Genome Biol 2001; 2(4):PREPRINT0003.

Liu Q, Wang L, Frutos A G, Condon A E, Corn R M and Smith L M. DNA computing on surfaces. Nature 2000 Jan. 13; 403(6766):175-9.

Natale D A, Shankavaram U T, Galperin M Y, Wolf Y I, Aravind L and Koonin E V. Towards understanding the first genome sequence of a crenarchaeon by genome annotation using clusters of orthologous groups of proteins (COGs). Genome Biol 2000; 1(5):RESEARCH0009.

Neapolitan R E. Probabilistic Reasoning in Expert Systems: Theory and Algorithms. New York: Wiley-Interscience; 1990.

Pearl J. Probabilistic Reasoning in Intelligent Systems: Networks of Plausible Inference. San Mateo, Calif.: Morgan-Kauffman; 1988.

Rumeihart D E, McClelland J L and PDP Research Group. Parallel Distributed Processing, Volume 1: Foundations. Cambridge, Mass.: MITPress; 1988.

Tatusov R L, Natale D A, Garkavtsev I V, Tatusova T A, Shankavaram U T, Rao B S, Kiryutin B, Galperin M Y, Fedorova N D and Koonin E V. The COG database: new developments in phylogenetic classification of proteins from complete genomes. Nucleic Acids Res 2001 Jan. 1; 29(1):22-8.

Woese C R. Interpreting the universal phylogenetic tree. Proc Natl Acad Sci USA 2000 Jul. 1 8; 97(15):8392-6.

Example 10

Use of Nonspecific DNA Amplification and DNA Microarray Technology for the Genetic Characterization of Environmental Backgrounds Introduction The ability to characterize the background biological profile of any given environment is essential if one wants to make evaluations relative to the perturbation of that system. Recent efforts using fluorescence excitation and emission data have demonstrated fluctuations of a factor often of the biological component of an air stream at a fixed outside location. The greatest variability is evident at the shorter duration interrogations. These significant variations are attenuated when one averages the data over increasing periods of time. It is important to note that these measurements look only at fluorescence and are unable to provide any information relative to the identity of biological species. There exists a technology void in the area of rapid, multi-dimensional characterization of background environmental fluctuations in biological species. Because of the wide diversity of airborne organisms, a technology must be developed that can definitively identify and characterize hundreds of biological species within a short time period at a reasonable cost.

Current technologies, to include organism-specific PCR and extensive clinical laboratory procedures, can provide this level of information. However, the cost and the time requirements for this extensive analysis is prohibitive. Costs for extensive characterization (greater than ten organisms) is well in excess of $10,000 per data point. We propose a new technology that leverages the substantial investments from both government and industry for the identification and characterization of diverse environmental samples. This technology combines the polymerase chain reaction (PCR) mechanism of DNA amplification and the more recently developed gene chip, or microarray, technologies. Our unique combination of these two disciplines will allow one to ask hundreds of thousands of questions regarding the nucleic acid content of environmental samples.

BACKGROUND

Polymerase Chain Reaction (PCR) is a licensed technology for the amplification of DNA. Generally this technique is used to amplify one or two specific regions of DNA from a target organism for later analysis. Used in this manner, the system can detect a single copy of DNA among billions of other segments of DNA of equal size. The specificity of this amplification is determined by the nucleic acid sequence of the primers, or starting templates for the amplification. These primers are usually on the order of 20-25 nucleic acids in length. The longer the length, the greater the specificity. Another method for the amplification of DNA within a given sample is the use of "random primers." Random primers are generally four to six bases in length. This short size results in practically all of the DNA within a given sample to be amplified. This amplification is nonspecific.

DNA arrays are constructed by two distinct technologies. The result is a gridded array of thousands of specific DNA sequences immobilized either on glass or membrane within a square centimeter. Affymetrix patented technology synthesizes the DNA chain directly linked to the glass slide. Laws of physics prevent them from constructing arrays with many more than 20 bases in length. The other approach is to spot small volumes of a solution containing DNA onto the slide or membrane. The DNA is then immobilized and denatured to allow hybridization. Using these technologies, investigators have patterned thousands of DNA sequences representing thousands of genes on single chips. The preponderance of literature and patents are on the use of these gene chips to identify gene regulation as a function of external stress or disease condition. Thus far, PCR is generally used to amplify either specific regions of DNA, or to make complimentary DNA to messenger RNA within a cell as an indicator of what genes are active. The gene chips are then used to determine the expression patterns.

Current state-of-the-art detection and identification of biological species is conducted either with PCR or antibody detection systems. PCR based systems use specific primers and probes to ask very specific questions about the target organisms. Even with advanced multiplexing, generally only one organism is targeted per reaction tube. Antibody systems also are targeting a limited number of epitopes and organisms. Antibody detection of organisms is hindered by lack of sensitivity and specificity.

Conventional wisdom uses the PCR system to amplify very specific regions of DNA. We propose to use the PCR system to amplify all DNA in the sample. The exact sensitivity in complex backgrounds will have to be established experimentally. The concept of using PCR for total DNA amplification is novel in the area of unknown identification.

DNA amplification and labeling will be accomplished by using Polymerase Chain Reaction (PCR) technology. PCR is a licensed technology generally used for the amplification of specific unique regions of DNA. Generally this technique is used to amplify one or two specific regions of DNA from a target organism for analysis. Used in this manner, the system can detect a single copy of DNA among billions of DNA fragments of equal size. The specificity of this amplification is determined by the nucleic acid sequence of the primers, or starting templates, for the amplification. These primers are usually on the order of 20-25 nucleic acids in length. The longer the length, the greater the specificity.

Another method for the amplification of DNA within a given sample is the use of "random primers." Random primers are generally four to six bases in length. This short size results in nonspecific amplification of essentially all DNA present in the sample. Our idea also includes the incorporation of a "labeled" nucleotide into the amplified DNA. This label will be either a molecule such as biotin, which can bind tightly to a reporter enzyme, or a fluorescent molecule. These tags will be used to identify amplified DNA sequences that specifically bind to our DNA microarray identification chip.

DNA arrays are constructed using two distinct technologies. The result is a gridded array of thousands of specific DNA sequences immobilized either on glass or opaque membrane within a square centimeter. Affymetrix has patented technology to synthesize the DNA chain directly linked to the glass slide. Laws of physics prevent them from constructing arrays with many more than 25 bases in length. Another approach is to spot small volumes of a solution containing DNA onto the slide or membrane. The DNA is then immobilized and denatured to allow hybridization. Using these technologies, investigators have patterned thousands of DNA sequences representing thousands of genes on single chips. The preponderance of literature is on the use of these gene chips to study gene regulation as a function of external stress or disease condition.

Our technological approach allows for the detection and identification of hundreds to thousands of specific species within a single sample. This represents a significant enhancement over current protocols. Our random primer PCR/DNA chip identification approach can be used for identification of bacteria and/or viruses in the environment. The technology is robust. A key strength of the proposed system is the ability to answer hundreds of broad and specific questions about the DNA in a sample. This allows us to employ a phylogenetic approach to identification, thereby dramatically improving our identification capabilities. This will enable us to perform broad background characterizations, to detect novel agents, and to provide partial answers to identify organisms related to a particular class of virus or bacteria as determined by the phylogenetic pattern. This is critical in the case of unknown or unexpected pathogens or when biological agents are suspected of being present in the environment. Current technology is directed at a limited number of organisms suspected of being attractive as BW agents. Our technology can identify those agents as well as many others.

Current identification systems can only identify a very limited number of organisms in near-real time. Our novel approach will enable us to positively identify hundreds of pathogens in minutes using a single microarray, or DNA chip. Moreover, by producing a hierarchical array of DNA fragments, some of which are highly conserved among species and others which are unique to particular species or strains of pathogens, our system will provide partial identification or background characterization. In short, this system can provide a detailed characterization of environmental samples in minutes that can currently only be achieved in the laboratory in days to weeks. The benefit of our identification system is a dramatic improvement in environmental characterization, a critical element for understanding the occurrence and nature of a biological perturbation of the environment.

We propose to develop a prototype microarray, or DNA chip, on membranes of glass for the identification of multiple biological species in environmental samples. Our approach will allow us to detect, in a single assay system, what currently requires hundreds of individual assays. Our prototype system will be composed of one reaction tube in which we will amplify all DNA present and incorporate a molecular tag into all amplified DNA in an environmental sample. The amplified/tagged DNA will then be exposed to a microarray, or DNA chip, containing hundreds of DNA fragments that can answer broad, as well as specific, questions about the identity of the DNA present in the sample. Matching DNA fragments from the amplified sample will be captured (hybridize) on specific areas of the DNA chip and an additional reagent will form a colored precipitate or other detectable optical signal. Off-the-shelf hardware and software will be used to read and interpret the pattern of spots that identify what organisms are present in the sample. This system will provide the capability to identify up to hundreds of species from a single sample within 30 minutes.

We will take a hierarchical approach to agent identification. We plan to spot DNA chips with known DNA sequences. We will have regions of the chip containing highly conserved regions of DNA, as well as unique regions. For example, *Bacillus anthracis* DNA would hybridize to a generic bacterial DNA spot, it would not hybridize to a human specific region, or a virus specific region. This amplified DNA would also bind to a *Bacillus* specific region, but not to a unique Bacillis gk~bigiisequence. It would bind to regions specific for *Bacillus anthracis*. The requirement for multiple positive hybridization regions decreases the probability of false positive readings.

PCR has generally been used to amplify either specific regions of DNA, or to make complimentary DNA to messenger RNA within a cell as an indicator of what genes are active. Gene chips have been used to determine cellular expression patterns and to detect single point mutations. The novel elements of our invention are random amplification of all DNA in a sample and a phylogenetic approach to identification using gene chip technology to provide much a broader biological identification capability than is currently available.

Current state-of-the-art detection and identification of biological pathogens is conducted either with PCR or antibody detection systems. PCR based systems use specific primers and probes to ask very specific questions about the target organisms. Even with advanced multiplexing, generally only one organism is targeted per reaction tube. Antibody systems also are targeting a limited number of epitopes and organisms. Antibody detection of organisms is hindered by lack of sensitivity and specificity.

The second portion of this invention is the construction of a gene chip micro-array on either an opaque membrane or glass slide. The chip will use published sequences of DNA for target pathogens, as well as common biological species. The ability to make thousands of spots will allow the specificity of hundreds to thousands of biological species on a single chip. The chip will then be incubated with the amplified, tagged DNA and allowed to hybridize. The DNA arrays on membranes using an enzymatic reaction to develop a colored precipitate will be less expensive and more portable than those based on glass slides using fluorescent tags. The membrane arrays, will specifically bind the biotinylated DNA from biological targets of interest. After hybridization, the chip will be washed and incubated with an avadin-linked colorimetric enzyme, such as glucose oxidase or horseradish peroxidase, which yield a colored product that forms a precipitate in the region of the hybridized DNA. The avadin binds biotin and localizes the enzyme only to the regions containing the amplified biotin-containing DNA. The advantage of using a glass substrate for the DNA chip is that a much higher density of DNA sequences can be assessed. The fluorescently tagged DNA will be hybridized and analyzed using a fluorescent array detection system.

The array will also be constructed to provide broad as well as specific identification. For example, 16s ribosomal DNA will be used to establish the presence of bacteria, conserved *bacillus* sequences will be used to identify *bacillus* presence, and specific DNA will further classify the *bacillus* species or strain. All of these hybridizations should be positive if the target organism is present in the sample.

We believe that our novel pathogen identification technology will have utility in health care, national security, homeland emergency response, and battlefield defense. We foresee the use of our random primer PCRJDNA chip identification devices in doctors' offices, clinics, and emergency rooms for identification of bacteria and/or viruses from throat and nasal swabs. A key strength of the proposed system is the ability to answer hundreds of broad and specific questions about the DNA in a sample. This allows us to employ a phylogenetic approach to identification, thereby dramatically improving our identification capabilities.

How Our Approach is Different

Microorganisms are currently identified by one of three methods. The "gold standard" is laboratory culture and microbiological characterization using specific growth and nutrient conditions. These methods take days to complete. Immunoassay methods involve recognition of a unique element (epitope) on the cell surface of the organism of interest using an "primary" antibody that is specific for that element. A "secondary" antibody with an attached molecular tag is generally bound to the primary antibody so that the specific interaction between the primary antibody and the organism of interest can be visualized. This process can yield a result in 10-25 minutes but the number of reliable antibodies to organisms of interest is very limited (a few dozen at most.) The third method is identification of specific genetic sequences that are unique to the organism(s) of interest.

The most common and frequently patented method of nucleic acid sequence detection and identification is via the polymerase chain reaction (PCR). This method requires that one know the target sequence. Primer pairs (generally 20-25 bases in length) are constructed to bracket the sequence of interest. Each primer pair and amplification reaction is optimized to amplify one unique region of the genome of the target organism a million times or more. Identification of an organism is generally based on one to five sequences of one to two hundred bases in length. In most instances, a different reaction tube is needed per primer pair. Therefore, identification of ten organisms can require as many as fifty separate reaction conditions, each reaction tube optimized for a specific genetic sequence.

In stark contrast, we will use much shorter primer pairs (four to six bases in length) as the start points for DNA amplification. These "random primers" bind to many regions of the genome. One of the four bases that are used to produce new DNA in the amplification reaction is tagged with a label that is used to visualize the amplified DNA. By adjusting the concentration of primers, the amount of template DNA, and other experimental parameters, we will generate a mixture of 100-500 base pair fragments that represent the entire genome of all of the biological species present in a sample. We expect to achieve 1000-10,000 fold amplification of DNA sequences with the ratio amplified DNA in direct proportion to the starting ratios. This is in stark contrast to standard PCR that produces millions of copies of a single sequence. This level of amplification should be sufficient as our method will be used evaluate clinical and environmental samples that contain a large number of target sequences. The exact level of sensitivity of our system has to be determined experimentally.

Once the labeled DNA sequences are generated, they will be exposed to our gene-chip. In general, gene-chip technology is being used to monitor and evaluate gene expression in a single organism or tissue. Thousands of genes or gene sequences are spotted on a chip. Genetic sequences expressed in the experimental condition are compared to expression in the control. In contrast, we will use gene chip technology to identify a wide variety of biological organisms. Our approach is not limited to expressed gene sequences. There may be many coding as well as non-coding regions of the genome that can be used to identify organisms of interest. Our system will contain genetic sequences that are found in essentially all living organisms as well as more specific sequences that are common to particular classes of organisms as well as sequences that are unique to a particular organism. Using this "phylogenetic tree", each spot on the chip will answer a specific question relative to the presence of that target sequence in the starting material.

The pattern of spots will indicate the presence of particular organisms. There are essentially four categories of genetic sequences from our standpoint. Sequences in the open literature, sequences maintained by the US Government, sequences patented by industry, and sequences that have not yet been determined. We do not intend to initiate a grand sequencing effort to identify target sequences. Many of the conserved sequences for large classes of organisms are already in the open literature and therefore available for our use. Significant numbers of unique sequences for organisms of interest are also in the open literature and available for use. With Government sponsorship, we can use unique sequences of pathogens identified by past, current and future Government sponsored efforts. Some sequences have been, and will continue to be patented, but this represents a very small proportion of the genetic sequence available for identification. If necessary, we can license or team to gain access to these sequences. Likewise, we can team with sequencing groups to determine unknown sequences. In short, there is enough DNA for everybody.

Various preferred embodiments of the invention have been described in fulfillment of the various objects of the invention. It should be recognized that these embodiments are merely illustrative of the principles of the invention. Numerous modifications and adaptations thereof will be readily apparent to those skilled in the art without departing from the spirit and scope of the present invention.

What is claimed is:

1. A method of monitoring water contamination, comprising,
   (a) combining nucleic acid molecules having one or more nucleic acid sequences and that are from at least one sample of water, with multiple oligonucleotide primers, wherein the primers comprise randomized nucleotide sequences;
   (b) amplifying the water sample nucleic acid molecules that hybridize to the randomized primers by subjecting the mixture of combined primers and sample nucleic acid molecules to a plurality of cycles of the polymerase chain reaction to generate an amplification product comprising a population of amplified nucleic acid molecules, wherein the primers are sufficiently randomized such that substantially all of the nucleic acid sequences of a biological entity in the water sample are represented among the amplified nucleic acid molecules;
(c) hybridizing the amplified nucleic acid molecules to an array of nucleic acid molecules having predetermined nucleic acid sequences, such that at least a portion of the amplification product hybridizes to the array, and wherein the array comprises redundancies comprising several distinct nucleic acid sequences from the same biological entity; and
(d) detecting the amplified nucleic acid molecules that hybridize to the array and relating the detected amplified nucleic acid molecules to at least one biological entity in the at least one sample of water.

2. A method monitoring water contamination, comprising,
(a) combining nucleic acid molecules having one or more nucleic acid sequences and that are from at least one sample of water, with multiple oligonucleotide primers, wherein the primers comprise randomized nucleotide sequences;
(b) amplifying the water sample nucleic acid molecules that hybridize to the randomized primers by subjecting the mixture of combined primers and sample nucleic acid molecules to a plurality of cycles of the polymerase chain reaction to generate an amplification product comprising a population of amplified nucleic acid molecules, wherein the primers are sufficiently randomized such that substantially all of the nucleic acid sequences of a biological entity in the water sample are represented among the amplified nucleic acid molecules;
(c) hybridizing the amplified nucleic acid molecules to an array of nucleic acid molecules having predetermined nucleic acid sequences, such that at least a portion of the amplification product hybridizes to the array, and wherein the array comprises positive controls, negative controls, and redundancies comprising several distinct nucleic acid sequences from the same biological entity, and wherein each of the predetermined nucleic acid sequences comprises a predetermined position on the array; and
(d) detecting the amplified nucleic acid molecules that hybridize to the array and relating the detected amplified nucleic acid molecules to at least one biological entity in the at least one sample of water.

3. The method of claim 1, wherein at least a portion of the nucleic acid molecules immobilized on the array each characterize a separate and distinct biological entity or a variant of a single biological entity.

4. The method of claim 1, wherein a detectable label is incorporated in the amplified nucleic acid molecules during amplification.

5. The method of claim 1, further comprising correlating the detected amplified nucleic acid molecules to at least one biological entity in the sample based on a pattern of hybridization of the amplified nucleic acid molecules to the array.

6. The method of claim 1, wherein the primers are four to fifteen, four to eight or six to eight nucleotides in length.

7. The method of claim 1, wherein the array of nucleic acid molecules having predetermined nucleic acid sequences are immobilized on a substantially planar surface, wherein each of the nucleic acid molecules having an individual predetermined nucleic acid sequence comprises a predetermined position on the array, and wherein at least a portion of the nucleic acid molecules immobilized on the array each characterize a separate and distinct biological entity or a variant of a single biological entity.

8. The method of claim 1, wherein the nucleic acid molecules having predetermined nucleic acid sequences are more than 30 nucleotides in length.

9. The method of claim 1, wherein the array of nucleic acid molecules having predetermined nucleic acid sequences comprises a plurality of branch points of at least one phylogenetic tree.

10. The method of claim 1, wherein two or more of the predetermined nucleic acid sequences are overlapping sequences.

11. The method of claim 1, wherein the array of nucleic acid molecules having predetermined nucleic acid sequences comprises genealogical information about at least one biological entity.

12. The method of claim 11, wherein the array of nucleic acid molecules having predetermined nucleic acid sequences comprises information regarding at least one of the genealogical criterion selected from the group consisting of a kingdom, a phylum, a class, an order, a family, a genus, and a species for at least one biological entity in the sample.

13. The method of claim 1, wherein the array of nucleic acid molecules having predetermined nucleic acid sequences comprises a continuum of sequences that range from sequences that are conserved among a plurality of organisms to sequences that are specific to one organism.

14. The method of claim 1, wherein at least two of the predetermined nucleic acid sequences comprise partial sequence identity.

15. The method of claim 1, wherein the water sample comprises multiple biological entities, the method further comprising simultaneous detection of two or more biological entities in the water sample being analyzed.

16. The method of claim 1, wherein a pattern recognition algorithm is used to correlate a pattern of hybridization to at least one biological entity in the water sample.

17. The method of claim 16, wherein the algorithm analyzes oligomer hybridization probability data.

18. The method of claim 17, further comprising using artificial neural networks to analyze the oligomer hybridization probability data.

19. The method of claim 17, further comprising using Bayesian Interference Nets to analyze the oligomer hybridization probability data.

20. The method of claim 1, wherein the redundancies on the array comprise more than one distinct nucleic acid sequence from a predetermined organism.

21. The method of claim 1, wherein the hybridization of the amplified nucleic acid molecules to the array provides the ability to extract information about the resistance of the biological entity to an antibiotic.

* * * * *